United States Patent [19]
Brocchini et al.

[11] Patent Number: 5,902,812
[45] Date of Patent: *May 11, 1999

[54] PHARMACEUTICAL PIPERAZINE COMPOUNDS

[75] Inventors: Stephen James Brocchini, Highland Park, N.J.; Justin Stephen Bryans; Adrian John Folkes, both of Slough, United Kingdom; Christopher John Latham; Julie Elizabeth Brumwell, both of Slough, United Kingdom

[73] Assignee: Xenova Limited, United Kingdom

[ * ] Notice: This patent is subject to a terminal disclaimer.

[21] Appl. No.: 08/693,173

[22] PCT Filed: Feb. 14, 1995

[86] PCT No.: PCT/GB95/00299

§ 371 Date: Sep. 24, 1996

§ 102(e) Date: Sep. 24, 1996

[87] PCT Pub. No.: WO95/21829

PCT Pub. Date: Aug. 17, 1995

[30] Foreign Application Priority Data

Feb. 14, 1994 [GB] United Kingdom ............... 9402806
Feb. 15, 1994 [GB] United Kingdom ............... 9402889

[51] Int. Cl.$^6$ .................. A61K 31/495; C07D 241/02; C07D 403/10; C07D 405/10
[52] U.S. Cl. ............... 514/253; 514/255; 544/373; 544/377; 544/385
[58] Field of Search ................. 544/373, 377, 544/385; 514/253, 255

[56] References Cited

FOREIGN PATENT DOCUMENTS

C 621862  11/1934  Germany.
94/04512  3/1994   WIPO ................... 544/385
WO A
9404513   3/1994   WIPO.

OTHER PUBLICATIONS

Wang et al, *Chinese Chemical Letters*, vol. 4 pp. 687–688, 1993.
Drug Evaluations by American Medical Association, pp. 745–746, 1993.

Kamel et al, Journal of Antiobiotics, vol. XLIII, pp. 1018–1020, 1990.
Yokol et al, Journal of Antiobiotics, vol. XLI, pp. 494–501, 1988.
Villemin et al, *Chemical Abstracts*, vol. 114, No. 185106, 1991.
Ricoh, Chemical Abstracts, vol. 97, No. 6, 1982 Columbus, Ohio, U.S.; abstract No. 40323s, p. 70.
Tetrahedron, (Incl. Tetrahedron Reports), vol. 47, No. 30, 1991, Oxford GB pp. 5643–5665, Th.T Shawe et al. Saframycin Synthetic Studies.; see p. 5645–p. 5653; example 8.
Chemical Abstracts vol. 65, 1966 16969—38–Heterocyclic Compounds 2,5–dioxopipeazines. II Reaction of 2,5–dioxopiperazine with aldehydes and nitroso compounds, Augustin.
The Lancet, Jul. 1987 pp. 3–8 Hamsten et al Plasminogen Activator Inhibitor in Plasma: Risk Factor for Recurrent Myocardial Infarction.
Circulation vol. 96 No. 3 Aug. 1997 pp. 916–921 Friederick et al Novel Low–Molecular–Weight Inhibitor of PAI–1 etc.
Thrombosis and Haemostasis 1996 pp. 808–815 Charlton et al Evaluation of a Low Molecular Weight etc.
Seminars in Thrombosis and Hemostasis vol. 18 No. 1, 1992 pp. 67–80 Krishnamurti et al Plasminogen Activator INhibitor Type 1: Biochemistry and Evidence for Modulation of Fibrinolysis in Vivo.

*Primary Examiner*—Emily Bernhardt
*Attorney, Agent, or Firm*—Nixon & Vanderhye

[57] ABSTRACT

Diketopiperazines of formula (A):

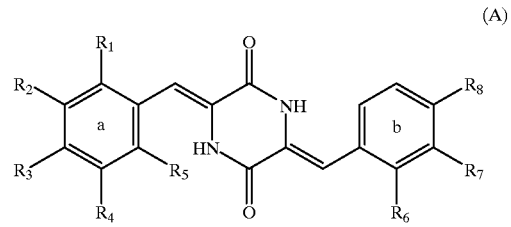

wherein each of $R_1$ to $R_8$ is H or an organic radical as described herein and the pharmaceutically acceptable salts thereof have activity as inhibitors of plasminogen activator inhibitor.

14 Claims, No Drawings

PHARMACEUTICAL PIPERAZINE COMPOUNDS

The present invention relates to compounds useful as inhibitors of plasminogen activator inhibitor (PAI), to their preparation and to pharmaceutical and veterinary compositions containing them.

Plasminogen activators (PAs) are serine proteases which control the activation of the zymogen, plasminogen, to the active enzyme plasmin. Plasmin is important in a number of physiological and pathological processes including fibrinolysis, tissue remodelling, tumour growth and metastasis. The glycoprotein plasminogen activator inhibitor (PAI) is an endogenous fast-acting inhibitor of PA activity. PAI is a member of the serpin family and is synthesized by a variety of cells including endothelial cells. An imbalance between PAs and PAI contributes to a number of pathological conditions including haemostasis, inflammation, tumour growth and metastasis.

The present invention provides a diketopiperazine of formula (A):

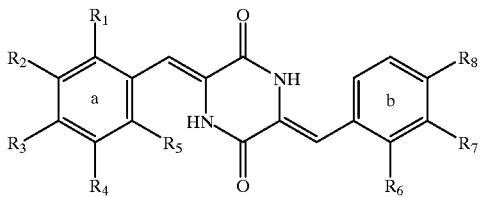

(A)

wherein $R_1$ is H, a halogen, —$COOR_{11}$, $C_1$–$C_6$ alkyl, $NO_2$, $C_1$–$C_6$ alkoxy, —$NHCOCH_3$ or $CF_3$;

$R_2$ is H, —$O(CH_2)_nN(R_{11}R_{12})$, $C_1$–$C_6$ alkyl, $NO_2$, CN, halogen, $C_1$–$C_6$ alkoxy, $CF_3$, $OCF_3$, —$NHCOCH_3$ or phthalimido;

$R_3$ is H, —$O(CH_2)_nN(R_{11}R_{12})$, halogen, $C_1$–$C_6$ alkoxy, $NO_2$, $C_1$–$C_6$ alkyl, $CF_3$, CN, —$CON(R_{11}R_{12})$, —$NHCOCH_3$, —$CO_2R_{11}$, —$CONH(CH_2)_nPh$, $SR_{13}$ or —$(CH_2)_nN(R_{11}R_{12})$; or $R_2$ and $R_3$ together form a methylenedioxy group —$OCH_2O$—;

$R_4$ is H, halogen, $NO_2$ or —$O(CH_2)_nN(R_{11}R_{12})$;

$R_5$ is H or a halogen;

$R_6$ is H, a halogen or —$O(CH_2)_nN(R_{11}R_{12})$;

$R_7$ is H, —$O(CH_2)_nN(R_{11}R_{12})$ or $C_1$–$C_6$ alkoxy; and $R_8$ is H, a halogen, —$O(CH_2)_nN(R_{11}R_{12})$, —$CH_2Y(CH_2)_n N(R_{11}R_{12})$, —$OC(O)(CH_2)_nR_{11}$, $C_1$–$C_6$ alkoxy, —$(CH_2)_nNHCO(CH_2)_nCO_2R_{11}$, —$(CH_2)_nN(R_{11}R_{12})$ —$CH_2N[(CH_2)_nN(R_{11}R_{12})]_2$, or —$O(CH_2)_n CO_2H$ wherein n is 0 or an integer of 1 to 6, Y is O or S, each of $R_{11}$ and $R_{12}$ is, independently, hydrogen or a straight or branched $C_1$–$C_6$ alkyl and $R_{13}$ is straight or branched $C_1$–$C_6$ alkyl; or a pharmaceutically acceptable salt or ester thereof; with the exception of compounds wherein (i) each of $R_1$ to $R_8$ is H;

(ii) $R_1$ and $R_6$ are both Cl or Br and the rest of $R_1$ to $R_8$ are H;

$R_3$ and $R_8$ are the same and are both F, Cl or OMe and the rest of $R_1$ to $R_8$ are H; and (iii) $R_8$ is OMe and the rest of $R_1$ to $R_{10}$ are H.

The numerals 1 to 10 denote ring positions on the phenyl groups in formula A. The letters a and b refer to the two phenyl rings themselves.

A $C_1$–$C_6$ alkyl group is typically a $C_1$–$C_4$ alkyl group, for example a methyl, ethyl, propyl, i-propyl, n-butyl, sec-butyl or tert-butyl group. A halogen is, for example, fluorine, chlorine, bromine or iodine.

A $C_1$–$C_6$ alkoxy group is typically a $C_1$–$C_4$ alkoxy group, for example a methoxy, ethoxy, propoxy, i-propoxy, n-butoxy, sec-butoxy or tert-butoxy group.

A group —$CH_2Y(CH_2)_nN(R_{11}R_{12})$ is preferably a group —$CH_2O(CH_2)_nNMe_2$ or —$CH_2S(CH_2)_nNMe_2$ wherein n is from 1 to 3.

In compounds of formula A free rotation may occur at room temperature about the single bonds connecting rings a and b to the double bonds at positions 3 and 6 of the piperazine-2,5-dione ring. Positions 2 and 6, and positions 3 and 5, in both rings a and b can therefore be considered as equivalent. As a consequence the following pairs of substituents can be viewed as interchangeable: $R_1$ and $R_5$; and $R_2$ and $R_4$.

Preferably one of rings a and b is unsubstituted or is mono-substituted whilst the other ring is unsubstituted or is substituted at one or more of positions 2 to 6. The ring which is mono-substituted may carry the substituent at any one of positions 2 to 6, for instance position 3 or 4, especially position 4. Thus for instance, when ring b is mono-substituted, one of $R_6$ to $R_8$ is other than hydrogen, preferably $R_7$ or $R_8$, especially $R_8$. When ring a is mono-substituted, one of $R_1$ to $R_5$ is other than hydrogen, preferably $R_2$ or $R_3$, especially $R_3$. When one of rings a and b is mono-substituted the substituent $R_1$ to $R_5$, or $R_6$ to $R_8$ respectively, is preferably selected from —$O(CH_2)_nN(R_{11}R_{12})$, especially —$O(CH_2)_2NMe_2$ or —$O(CH_2)_3NMe_2$; —$CH_2Y(CH_2)_nN(R_{11}R_{12})$; a halogen, for instance fluorine or chlorine; and an alkoxy group, for instance OMe.

When one of rings a and b is unsubstituted, or is mono-substituted as described in the above paragraph, the other ring may bear any desired substitution pattern. For instance, the other ring may be unsubstituted or may be mono-, di- or tri-substituted at any of positions 2 to 6 in the case of ring a, or at any of positions 2 to 4 in the case of ring b.

The said other ring may, for instance, be mono-substituted at any of positions 2 to 6, when it is ring a, or positions 2 to 4 when it is ring b. Ring a may also be 2,3-, 2,4-, 2,5-, 2,6-, 3,4- or 3,5-disubstituted, or 2,3,4-, 2,3,5-, 2,3,6- or 3,4,5-trisubstituted. Ring b may be 2,3 or 2,4 disubstituted, or 2,3,4-trisubstituted. Thus, when the said other ring is a and is mono-substituted, four of $R_1$ to $R_5$ are hydrogen and one is other than hydrogen. When the said other ring is ring a and is disubstituted, three of $R_1$ to $R_5$ are hydrogen and two are other than hydrogen. For example $R_1$ and $R_2$, or $R_1$ and $R_3$, or $R_1$ and $R_4$, or $R_1$ and $R_5$, or $R_2$ and $R_3$, or $R_2$ and $R_4$ are other than hydrogen whilst, in each case, the other three of $R_1$ to $R_5$ are hydrogen.

When the said other ring is ring a and is trisubstituted, two of $R_1$ to $R_5$ are hydrogen and three are other than hydrogen. For example, $R_1$, $R_2$ and $R_3$, or $R_1$, $R_2$ and $R_4$, or $R_1$, $R_2$ and $R_5$, or $R_2$, $R_3$ and $R_4$ are other than hydrogen whilst, in each case, the other two of $R_1$ to $R_5$ are hydrogen.

When the said ring is b and is mono-substituted, two of $R_6$ to $R_8$ are hydrogen and one is other than hydrogen. When the said other ring is b and is di-substituted, one of $R_6$ to $R_8$ is hydrogen and two are other than hydrogen. For example $R_6$ and $R_7$, or $R_6$ and $R_8$ are other than hydrogen. When the said other ring is b and is trisubstituted, all three of $R_6$ to $R_8$ are other than hydrogen.

In a preferred series of compounds of formula A each of $R_6$ and $R_7$ is hydrogen and $R_8$ is —$O(CH_2)_nN(R_{11}R_{12})$ or —$CH_2Y(CH_2)_nN(R_{11}R_{12})$ as defined above. In another preferred series of compounds, $R_8$ is —$O(CH_2)_nN(R_{11}R_{12})$, one of $R_6$ and $R_7$ is —$O(CH_2)_nN(R_{11}R_{12})$ or halogen and the other of $R_6$ and $R_7$ is H. Preferably —O(CH$_2$)$_n$N(R$_{11}$R$_{12}$) is —O(CH$_2$)$_2$NMe$_2$ or —O(CH$_2$)$_3$NMe$_2$.

In the above-mentioned series of preferred compounds $R_1$ to $R_5$ are all hydrogen, or one or two of $R_1$ to $R_5$ are other than hydrogen whilst the others are hydrogen. For instance one of $R_1$, $R_2$ and $R_3$ is other than hydrogen. Alternatively $R_1$ and $R_3$, or $R_2$ and $R_3$, are other than hydrogen.

Particularly preferred compounds are those wherein $R_8$ is —O(CH$_2$)$_n$NMe$_2$ or —CH$_2$Y(CH$_2$)$_n$N(R$_{11}$R$_{12}$) wherein n is 2 or 3, $R_6$ and $R_7$ and each of $R_1$ to $R_5$ is as specified above.

In one embodiment, $R_1$ is H, Cl Me, MeO, NO$_2$ or —COOMe;

$R_2$ is H, Me, MeO, Cl, Br or —O(CH$_2$)$_n$NMe$_2$; or $R_2$ and $R_3$ together form a methylenedioxy group —OCH$_2$O—;

$R_3$ is H, OCH$_3$, OC$_6$H$_{14}$, O(CH$_2$)$_n$NMe$_2$ wherein n is 2 or 3, or CH$_2$NMe$_2$;

$R_4$ is H or —O(CH$_2$)$_2$NMe$_2$;

$R_5$ is H or Cl;

$R_6$ is H, Cl or F or —O(CH$_2$)$_2$NMe$_2$;

$R_7$ is H, —O(CH$_2$)$_n$NMe$_2$ wherein n is 1 or 2, or OMe; and $R_8$ is H, F, OMe, —O(CH$_2$)$_n$NMe, —CH$_2$S(CH$_2$)$_n$NMe$_2$ or —CH$_2$O(CH$_2$)$_n$NMe$_2$ wherein n is 1, 2 or 3, —CH$_2$NHCO(CH$_2$)$_3$CO$_2$Me, —CH$_2$NH$_2$, —(CH$_2$)$_n$NMe$_2$ wherein n is 1, 2, 3 or 4; —OCH$_2$CO$_2$H, —CH$_2$N[(CH$_2$)$_3$NMe$_2$], or —OCO(CH$_2$)$_n$R$_{11}$ wherein n is from 1 to 5 and R$_{11}$ is CH$_3$ or t-butyl.

In a second embodiment $R^8$ is —O(CH$_2$)$_n$NMe$_2$ wherein n is 2 or 3, each of $R_6$ and $R_7$ is H; $R_1$ is H or Cl; $R_2$ is H, $R_3$ is H, C$_1$–C$_6$ alkoxy such as OMe, —O(CH$_2$)$_n$NMe$_2$ wherein n is 2 or 3, or —CH$_2$NMe$_2$; $R_4$ is H and $R_5$ is H or Cl.

In a further embodiment, $R_1$ is H, Cl or —COOMe; $R_2$, $R_3$ and $R_4$ are each independently H or —O(CH$_2$)$_n$NMe$_2$ wherein n is 1 or 2;

$R_5$ is H or Cl;

$R_6$ is H or F;

$R_7$ is H, OMe or —O(CH$_2$)$_n$NMe$_2$ wherein n is 1 or 2; and $R_8$ is H, F, or —O(CH$_2$)$_2$NMe$_2$.

In another embodiment $R_8$ and one of $R_6$ and $R_7$ is, independently, —O(CH$_2$)$_n$NMe$_2$ wherein n is 2 or 3, the other of $R_6$ and $R_7$ is H; and each of $R_1$ to $R_5$ is H.

In a further embodiment $R_8$ is —O(CH$_2$)$_n$NMe$_2$ wherein n is 2 or 3, $R_6$ is Cl and $R_7$ is H, or $R_6$ is H and $R_7$ is OMe; and each of $R_1$ to $R_5$ is H.

In a yet further embodiment each of $R_1$ to $R_5$ is H;

$R_6$ is H, —O(CH$_2$)$_n$NMe$_2$, Cl or F;

$R_7$ is H, —O(CH$_2$)$_n$NMe$_2$ wherein n is 1 or 2, or OMe; and $R_8$ is H, —OCOCH$_2$-$^t$Bu, —O(CH$_2$)$_n$NMe$_2$ wherein n is 1 or 2, —NCH$_2$NH$_2$, —CH$_2$N[(CH$_2$)$_3$NMe$_2$] or —OCH$_2$CO$_2$H.

Certain diketopiperazines have been disclosed as having utility as bioactive agents. Yokoi et al in J. Antibiotics vol XLI No. 4, pp 494–501 (1988) describe structure-cytotoxicity relationship studies on a series of diketopiperazines related to neihumicin, a compound obtained from the micro-organism *Micromonospora neihuensis*. Kamei et al in J. Antibiotics vol XLIII No. 8, 1018–1020 disclose that two diketopiperazines, designated piperafizines A and B, have utility as potentiators of the cytotoxicity of vincristine.

Examples of specific compounds of formula A are as follows. The compound numbering is adhered to in the rest of the specification:

1962 (3Z,6Z)-3,6-Di-(4-(2-dimethylaminoethoxy) benzylidene)- 2,5-piperazinedione dihydrochloride.

1953 (3Z,6Z)-3-Benzylidene-6-(4-bis(2-dimethylaminopropyl)aminomethylbenzylidene-2,5-piperazinedione.

1961 (3Z,6Z)-3-Benzylidene-6-(4-(2-dimethylaminoethoxy)benzylidene)-2,5-piperazinedione.

1957 (3Z,6Z)-3,6-Di-(4-(2-dimethylaminopropoxy) benzylidene)-2,5-piperazinedione bis methane sulfonate (1:2).

1949 (3Z,6Z)-3-Benzylidene-6-(3,4-di-(2-dimethylaminoethoxy)benzylidene)-2,5-piperazinedione.

1952 (3Z,6Z)-3-(2,6-Dichlorobenzylidene)-6-(4-(2-dimethylaminoethoxy)benzylidene-2,5-piperazinedione.

1955 (3Z,6Z)-3,6-Di-(4-(3-dimethylaminopropoxy) benzylidene)-2,5-piperazinedione bis hydrogen succinate (1:2).

1913 (3Z,6Z)-3-Benzylidene-6-(4-dimethylaminomethylbenzylidene)-2,5-piperazinedione.

1909 Methyl 4-(4-((3Z,6Z)-6-(4-Methoxybenzylidene)-2,5-dioxo-3-piperazinylidene)methylbenzylcarbonyl) butanoate.

1885 (3Z,6Z)-3-(4-(3,3-dimethylbutanoyloxy)benzylidene)-6-(4-methoxybenzylidene)-2,5-piperazinedione.

1665 (3Z,6Z)-3-(4-Acetamidobenzylidene)-6-(2-fluorobenzylidene)-2,5-piperazinedione.

1951 (3Z,6Z)-3-Benzylidene-6-(2-chloro-4-(2-dimethylaminoethoxy)benzylidene)-2,5-piperazinedione.

1969 (3Z,6Z)-3-Benzylidene-6-(2,4-di-(2-dimethylaminopropoxy)benzylidene)-2,5-piperazinedione.

1984 (3Z,6Z)-3-Benzylidene-6-(2,4-di-(2-dimethylaminoethoxy)benzylidene-2,5-piperazinedione.

1981 (3Z,6Z)-3-Benzylidene-6-(4-bis(3-dimethylaminopropyl)aminomethylbenzylidene)-2,5-piperazinedione.

1908 (3Z,6Z)-3-Benzylidene-6-(4-(2-dimethylaminoethoxy)benzylidene)-2,5-piperazinedione.

1977 (3Z,6Z)-3-(2,4-Difluorobenzylidene)-6-(4-(2-dimethylaminoethoxy)benzylidene)-2,5-piperazinedione.

1911 (3Z,6Z)-3-(4-(2-Dimethylaminoethoxy)benzylidene)-6-(4-methoxybenzylidene-2,5-piperazinedione.

1946 (3Z,6Z)-3-Benzylidene-6-(2-(2-dimethylaminoethoxy)benzylidene)-2,5-piperazinedione.

1924 (3Z,6Z)-3-Benzylidene-6-(4-(2-dimethylaminoethoxy)benzylidene)-2,5-piperazinedione.

1925 (3Z,6Z)-3-(4-Aminomethylbenzylidene)-6-benzylidene-2,5-piperazinedione trifluoroacetate.

1914 (3Z,6Z)-3-Benzylidene-6-(4-dimethylaminobenzylidene)-2,5-piperazinedione hydrochloride.

1907 (3Z,6Z)-3-(4-Hexyloxybenzylidene)-6-(4-methoxybenzylidene)-2,5-piperazinedione.

5233 (3Z,6Z)-3-(4-Chlorobenzylidene)-6-(4-(3-dimethylaminopropoxy)benzylidene-2,5-piperazinedione.

5236 (3Z,6Z)-3-(3,4-Dichlorobenzylidene)-6-(4-(3-dimethylaminopropoxy)benzylidene-2,5-piperazinedione.

5237 (3Z,6Z)-3-(3-Chlorobenzylidene)-6-(4-(3-dimethylaminopropoxy)benzylidene-2,5-piperazinedione.

5245 (3Z,6Z)-3-(4-Cyanobenzylidene)-6-(4-(3-dimethylaminopropoxy)benzylidene-2,5-piperazinedione.

5250 (3Z,6Z)-3-(4-Butoxybenzylidene)-6-(4-(3-dimethylaminopropoxy)benzylidene-2,5-piperazinedione.

5260 (3Z,6Z)-3-(4-Aminobenzylidene)-6-(4-(3-dimethylaminopropoxy)benzylidene-2,5-piperazinedione.
5348 (3Z,6Z)-3-(4-Cyanobenzylidene)-6-(4-(3-dimethylaminopropoxy)benzylidene-2,5-piperazinedione.
5360 (3Z,6Z)-3-(4-Bromobenzylidene)-6-(4-(3-dimethylaminopropoxy)benzylidene-2,5-piperazinedione.
5366 (3Z,6Z)-3-(4-Chlorobenzylidene)-6-(4-(3-dimethylaminopropoxy)benzylidene-2,5-piperazinedione.
5234 (3Z,6Z)-3-(4-(3-Dimethylaminopropoxy)benzylidene)-6-(4-methoxybenzylidene)-2,5-piperazinedione.
5235 (3Z,6Z)-3-(4-(3-Dimethylaminopropoxy)benzylidene)-6-(4-methylbenzylidene)-2,5-piperazinedione.
5238 (3Z,6Z)-3-(4-(3-Dimethylaminopropoxy)benzylidene)-6-(4-tert-butylbenzylidene)-2,5-piperazinedione.
5239 (3Z,6Z)-3-(4-(3-Dimethylaminopropoxy)benzylidene)-6-(4-trifluoromethylbenzylidene)-2,5-piperazinedione.
5365 (3Z,6Z)-3-(4-(3-Dimethylaminopropoxy)benzylidene)-6-(4-fluorobenzylidene)-2,5-piperazinedione.
5385 (3Z,6Z)-3-(4-(3-Dimethylaminopropoxy)benzylidene)-6-(4-methylthiobenzylidene)-2,5-piperazinedione.
5401 Methyl 4((3Z,6Z)-6-(4-(3-Dimethylaminopropoxy)benzylidene)-2,5-dioxo-3-piperazinylidene)methylbenzoate.
5246 4-((3Z,6Z)-6-(4-(3-Dimethylaminopropoxy)benzylidene)-2,5-dioxo-3-piperazinylidene)methylbenzamide.
5343 4-((3Z,6Z)-6-(4-(3-Dimethylaminopropoxy)benzylidene)-2,5-dioxo-3-piperazinylidene)methylbenzanilide.
5344 N-Benzyl-4-((3Z,6Z)-6-(4-(3-Dimethylaminopropoxy)benzylidene)-2,5-dioxo-3-piperazinylidene)methylbenzamide.
5345 N-Phenethyl-4-((3Z,6Z)-6-(4-(3-Dimethylaminopropoxy)benzylidene)-2,5-dioxo-3-piperazinylidene)methylbenzamide.
5346 N-(3-Phenylpropyl)-4-((3Z,6Z)-6-(4-(3-Dimethylaminopropoxy)benzylidene)-2,5-dioxo-3-piperazinylidene)methylbenzamide.
5347 N-(4-Phenylbutyl)-4-((3Z,6Z)-6-(4-(3-Dimethylaminopropoxy)benzylidene)-2,5-dioxo-3-piperazinylidene)methylbenzamide.
5186 (3Z,6Z)-6-(4-(3-Dimethylaminopropoxy)benzylidene)-3-(2-methylbenzylidene)-2,5-piperazinedione.
5187 (3Z,6Z)-6-(4-(3-Dimethylaminopropoxy)benzylidene)-3-(3-methylbenzylidene)-2,5-piperazinedione.
5201 (3Z,6Z)-6-(4-(3-Dimethylaminopropoxy)benzylidene)-3-(3,4-methylenedioxybenzylidene)-2,5-piperazinedione.
5208 (3Z,6Z)-6-(4-(3-Dimethylaminopropoxy)benzylidene)-3-(2-nitrobenzylidene)-2,5-piperazinedione.
5209 (3Z,6Z)-6-(4-(3-Dimethylaminopropoxy)benzylidene)-3-(3-nitrobenzylidene)-2,5-piperazinedione.
5210 (3Z,6Z)-6-(4-(3-Dimethylaminopropoxy)benzylidene)-3-(2-nitrobenzylidene)-2,5-piperazinedione.
5242 (3Z,6Z)-6-(4-(3-Dimethylaminopropoxy)benzylidene)-3-(3-methoxybenzylidene)-2,5-piperazinedione.
5241 (3Z,6Z)-6-(4-(3-Dimethylaminopropoxy)benzylidene)-3-(2-methoxybenzylidene)-2,5-piperazinedione.
5251 (3Z,6Z)-6-(4-(3-Dimethylaminopropoxy)benzylidene)-3-(2-trifluoromethylbenzylidene)-2,5-piperazinedione.
5252 (3Z,6Z)-6-(4-(3-Dimethylaminopropoxy)benzylidene)-3-(3-trifluoromethylbenzylidene)-2,5-piperazinedione.
5255 (3Z,6Z)-6-(4-(3-Dimethylaminopropoxy)benzylidene)-3-(3-phthalimidobenzylidene)-2,5-piperazinedione.
5373 (3Z,6Z)-6-(4-(3-Dimethylaminopropoxy)benzylidene)-3-(3-fluorobenzylidene)-2,5-piperazinedione.
5374 (3Z,6Z)-6-(4-(3-Dimethylaminopropoxy)benzylidene)-3-(3-trifluoromethoxybenzylidene)-2,5-piperazinedione.
5378 (3Z,6Z)-6-(4-(3-Dimethylaminopropoxy)benzylidene)-3-(3,5-dinitrobenzylidene)-2,5-piperazinedione.
5065 (3Z,6Z)-6-Benzylidene-3-(4-(2-diethylaminoethoxy)benzylidene-2,5-piperazinedione.
5070 (3Z,6Z)-3-(2-Bromobenzylidene)-6-(4-(2-dimethylaminoethoxymethyl)benzylidene)-2,5-piperazinedione.
5080 (3Z,6Z)-3-(2-Bromobenzylidene)-6-(4-(2-Dimethylaminoethylthiomethyl)benzylidene)-2,5-piperazinedione.
1634 Methyl 2-((3Z,6Z)-6-benzylidene-2,5-dioxo-3-piperazinylidene)methylbenzamide.
1852 (3Z,6Z)-6-Benzylidene-3-(4-(3-dimethylaminopropoxy)benzylidene)-2,5-piperazinedione.
1887 (3Z,6Z)-3-(4-Heptanoyloxybenzylidene)-6-(4-methoxybenzylidene)-2,5-piperazinedione.
1889 (3Z,6Z)-6-Benzylidene-3-(4-(3,3-dimethylbutanoyloxy)benzylidene)-2,5-piperazinedione.
1920 (3Z,6Z)-3-(4-Butoxybenzylidene)-6-(4-(3-dimethylaminopropoxy)benzylidene)-2,5-piperazinedione.
1947 (3Z,6Z)-3,6-Di-(3-(2-dimethylaminoethoxy)benzylidene)-2,5-piperazinedione.
1954 (3Z,6Z)-6-Benzylidene-3-(4-(2-dimethylaminoethoxy)benzylidene)-2,5-piperazinedione.
1978 (3Z,6Z)-6-Benzylidene-3-(3,4-di-(2-dimethylaminoethoxy)benzylidene)-2,5-piperazinedione.
1979 (3Z,6Z)-Benzylidene-3-(2-(2-dimethylaminoethoxy)benzylidene)-2,5-piperazinedione.
1980 (3Z,6Z)-3-(2,6-Dichlorobenzylidene)-6-(4-(2-dimethylaminoethoxy)benzylidene)-2,5-piperazinedione.
5060 (3Z,6Z)-3-(2-Bromobenzylidene)-6-(4-(3-dimethylaminopropoxy)benzylidene)-2,5-piperazinedione.
5249 (3Z,6Z)-3-(2-Chlorobenzylidene)-6-(4-(3-dimethylaminopropoxy)benzylidene)-2,5-piperazinedione.
5248 (3Z,6Z)-3-(2-Acetamidobenzylidene)-6-(4-(3-dimethylaminopropoxy)benzylidene-2,5-piperazinedione.
5256 (3Z,6Z)-3-(3-Acetamidobenzylidene)-6-(4-(3-dimethylaminopropoxy)benzylidene)-2,5-piperazinedione.
5372 (3Z,6Z)-3-(3,5-Dichlorobenzylidene)-6-(4-(3-dimethylaminopropoxy)benzylidene)-2,5-piperazinedione.

5375 (3Z,6Z)-3-(3-Bromobenzylidene)-6-(4-(3-dimethylaminopropoxy)benzylidene)-2,5-piperazinedione.

5398 (3Z,6Z)-3-(4-Chloro-3-nitrobenzylidene)-6-(4-(3-dimethylaminopropoxy)benzylidene)-2,5-piperazinedione.

5023 (3Z,6Z)-3-(4-Dimethylaminomethylbenzylidene)-6-(4-(3-dimethylaminopropoxy)benzylidene)-2,5-piperazinedione.

5048 (3Z,6Z)-3-(4-Acetamidobenzylidene)-6-(4-(3-dimethylaminopropoxy)benzylidene)-2,5-piperazinedione.

5068 (3Z,6Z)-3-(4-Dimethylaminobenzylidene)-6-(4-(3-dimethylaminopropoxy)benzylidene)-2,5-piperazinedione.

5232 (3Z,6Z)-3-(3-Cyanobenzylidene)-6-(4-(3-dimethylaminopropoxy)benzylidene)-2,5-piperazinedione.

1960 (3Z,6Z)-6-Benzylidene-3-(2-chloro-4-(2-dimethylaminoethoxy)benzylidene)-2,5-piperazinedione, hydrochloride.

5228 (3Z,6Z)-3-(4-(3-dimethylaminopropoxy)benzylidene)-6-(4-nitrobenzylidene)-2,5-piperazinedione.

5058 (3Z,6Z)-6-Benzylidene-3-(4-(2-Dimethylaminoethylthiomethyl)benzylidene)-2,5-piperazinedione.

Compounds of formula A may be prepared by a process which comprises either (i) condensing a compound of formula (I)

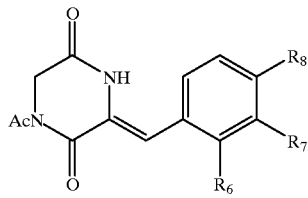

(I)

wherein $R_6$ to $R_{10}$ are as defined above and are optionally protected, with a compound of formula (II):

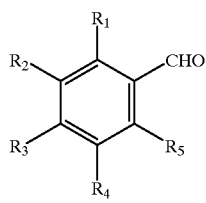

(II)

wherein $R_1$ to $R_5$ are defined above and are optionally protected, in the presence of a base in an organic solvent; or (ii) condensing a compound of formula (I'):

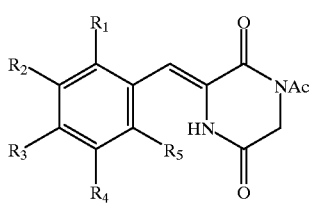

(I')

wherein $R_1$ to $R_5$ are as defined above and are optionally protected, with a compound of formula (III):

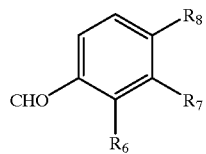

(III)

wherein $R_6$ to $R_{10}$ are as defined above and are optionally protected, in the presence of a base in an organic solvent; and, in either case (i) or (ii), if required, removing optionally present protecting groups and/or, if desired, converting one compound of formula A into another compound of formula A, and/or, if desired, converting a compound of formula A into a pharmaceutically acceptable salt or ester thereof, and/or, if desired, converting a salt or ester into a free compound, and/or, if desired, separating a mixture of isomers of compounds of formula A into the single isomers.

A compound of formula A produced directly by the condensation reaction between (I) and (II) or (I') and (III) may be modified, if desired, by converting one or more of groups $R_1$ to $R_{10}$ into different groups $R_1$ to $R_{10}$. These optional conversions may be carried out by methods known in themselves. For example, a compound of formula A in which $R_1$ is an ester group may be converted to a compound of formula A wherein the corresponding substituent is a free —COOH group, by acid or alkaline hydrolysis at a suitable temperature, for example from ambient temperature to 100° C.

A compound of formula A in which $R_1$ is a —$CO_2H$ group may be converted into a compound of formula A wherein $R_1$ is esterified by esterification, for example by treating the carboxylic acid with a suitable $C_1$–$C_6$ alkyl alcohol in the presence of 1,3-dicyclohexylcarbodiimide in an inert solvent.

Protecting groups for $R_1$ to $R_8$ in any of the compounds of formulae (I), (I'), (II) and (III) are optionally introduced prior to step (i) or step (ii) when any of groups $R_1$ to $R_8$ are groups which are sensitive to the condensation reaction conditions or incompatible with the condensation reaction, for example a —COOH or amino group. The protecting groups are then removed at the end of the process. Any conventional protecting group suitable for the group $R_1$ to $R_8$ in question may be employed, and may be introduced and subsequently removed by well-known standard methods.

The condensation reaction between compounds (I) and (II) or (I') and (III) is suitably performed in the presence of a base which is potassium t-butoxide, sodium hydride, potassium carbonate, sodium carbonate, caesium carbonate, sodium acetate, potassium fluoride on alumina, or triethylamine in a solvent such as dimethylformamide, or in the presence of potassium t-butoxide in t-butanol or a mixture of t-butanol and dimethylformamide. The reaction is typically performed at a temperature from 0° C. to the reflux temperature of the solvent.

The compounds of formula (I) may be prepared by a process comprising reacting 1,4-diacetyl-2,5-piperazinedione with a compound of formula (III) as defined above, in the presence of a base in an organic solvent. Similarly, the compounds of formula (I') may be prepared by a process which comprises reacting 1,4-diacetyl-2,5-piperazinedione with a compound of formula (II) as defined above, in the presence of a base in an organic solvent.

If necessary, the resulting compound of formula (I) or (I') can be separated from other reaction products by chromatography.

The reaction of 1,4-diacetyl-2,5-piperazinedione with the compound of formula (III) or (II) is suitably performed under the same conditions as described above for the condensation between compounds (I) and (II), or (I') and (III).

The substituted benzaldehydes of formulae (II) and (III) are known compounds or can be prepared from readily available starting materials by conventional methods. The 1,4-diacetyl-2,5-piperazinedione used as a starting material in the preparation of compounds of formula (I) may be prepared by treating 2,5-piperazinedione (glycine anhydride) with an acetylating agent. The acetylation may be performed using any conventional acetylating agent, for example acetic anhydride under reflux or, alternatively, acetic anhydride at a temperature below reflux in the presence of 4-dimethylaminopyridine.

Compounds of formula (I) may also be prepared by the microwave irradiation of a mixture comprising 1,4-diacetyl-2,5-piperazinedione, a compound of formula (III) and potassium fluoride on alumina (as base) in the absence of solvent.

Compounds of formula (I) may alternatively be prepared directly from 2,5-piperazinedione (glycine anhydride) by a process which comprises treating the 2,5-piperazinedione with a mixture comprising a compound of formula (III), sodium acetate and acetic anhydride at an elevated temperature, for example under reflux.

Compounds of formula (I') may be prepared by analogous processes, replacing compound (III) in each case by a compound of formula (II).

Compounds of formula A may also be prepared by a process comprising the microwave irradiation of (i) a mixture comprising a compound of formula (I) as defined above, a compound of formula (II) and potassium fluoride on alumina, or (ii) a mixture comprising a compound of formula (I') a compound of formula (III) and potassium fluoride on alumina, or (iii) a mixture comprising 1,4-diacetyl-2,5-piperazinedione, a compound of formula (II), a compound of formula (III) and potassium fluoride on alumina. The irradiation is performed in the absence of a solvent.

Compounds of formula (A) may also be obtained directly by a process which comprises condensing together 1,4-diacetyl-2,5-piperazinedione, a compound of formula (II) and a compound of formula (III) in the presence of a base in an organic solvent. Suitable bases, solvents and reaction conditions are as described above for the condensation reaction between, for example, compounds (I) and (II).

An alternative direct process for the preparation of compounds of formula (A) comprises condensing together 2,5-piperazinedione, a compound of formula (II) and a compound of formula (III) in the presence of sodium acetate and acetic anhydride at elevated temperature, for example under reflux.

An alternative process for the preparation of compounds of formula (I) comprises treating a compound of formula (V):

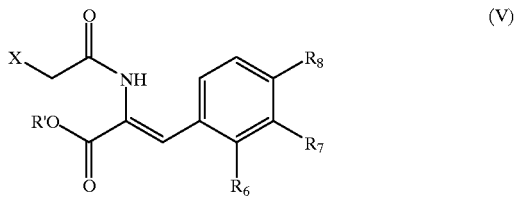

(V)

wherein $R_6$ to $R_8$ are as defined above, X is a halogen and R' is a $C_1$–$C_6$ alkyl group, with ammonia followed by acetic anhydride.

Compounds of formula (I') may be prepared by an analogous process which comprises treating a compound of formula (V'):

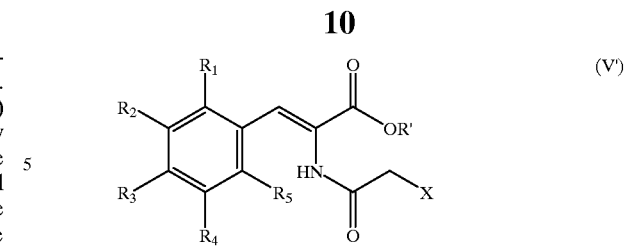

(V')

wherein $R_1$ to $R_5$, X and $R^1$ are as defined above, with ammonia followed by acetic anhydride.

X in formula (V) or (V') is typically iodine. $R^1$ is, for example, a $C_1$–$C_4$ alkyl group such as a methyl, ethyl, propyl, i-propyl, butyl, sec-butyl or tert-butyl group.

A review of synthetic approaches to unsaturated 3-monosubstituted and 3,6-disubstituted-2,5-piperazinediones is provided in Heterocycles, 1983, 20, 1407 (C.Shin).

Compounds of formula (A) may be converted into pharmaceutically acceptable salts, and salts may be converted into the free compound, by conventional methods. Suitable salts include salts with pharmaceutically acceptable, inorganic or organic, bases, or pharmaceutically acceptable inorganic or organic acids. Examples of inorganic bases include ammonia and carbonate, hydroxides and hydrogen carbonates of group I and group II metals such as sodium, potassium, magnesium and calcium. Examples of organic bases include aliphatic and aromatic amines such as methylamine, triethylamine, benzylamine, dibenzylamine or α- or β-phenylethylamine, and heterocyclic bases such as piperidine, 1-methylpiperidine and morpholine. Examples of inorganic acids include hydrochloric acid, sulphuric acid and orthophosphoric acid. Examples or organic acids include p-toluenesulphonic acid, methanesulphonic acid, mucic acid and butan-1,4-dioic acid.

Compounds of formula (A) may also be converted into pharmaceutically acceptable esters. Suitable esters include branched or unbranched, saturated or unsaturated $C_1$–$C_6$ alkyl esters, for example methyl, ethyl and vinyl esters.

Preferred compounds of formula A are depicted by means of their substitution patterns in Table 1 which follows. The compound numbering is adhered to in the rest of the specification. Characterising data for the compounds are set out in Table 2 in Example 16.

The diketopiperazines of formula (A) and their pharmaceutically acceptable salts and esters (referred to hereinafter as the "present compounds") have utility as inhibitors of PAI. Elevated levels of PAI-1, by reducing the net endogenous fibrinolytic capacity, can contribute to the pathogenesis of various thrombotic disorders including myocardial infarction, deep vein thrombosis and disseminated intravascular coagulation. The present compounds therefore can act as inhibitors of the tPA/PAI-1 interaction. The present compounds can be used in the treatment of haemostatic disorders. A human or animal, e.g. a mammal, can therefore be treated by a method comprising administration of a therapeutically effective amount of a diketopiperazine of formula (A) or a pharmaceutically or veterinarily acceptable salt thereof.

Tissue plasminogen activator (tPA) is used as a fibrinolytic agent in the treatment of thrombotic disorders. The efficacy of the tPA in this role may be enhanced if it is administered together with a PAI inhibitor. A human or animal, e.g. a mammal, can therefore be treated by a method comprising the combined administration of a therapeutically effective amount of tPA and a therapeutically effective amount of any one of the present compounds. The present invention also provides products containing a diketopiperazine of formula (A) or a pharmaceutically acceptable salt or ester thereof and tPA as a combined preparation for simultaneous, separate or sequential use in the treatment of thrombotic disorders, for example where there is inappropriate PAI activity. In such products the present compound is formulated for oral or parenteral (intravenous, intramuscular or subcutaneous) administration and the tPA is formulated for intravenous administration.

As one example, during acute myocardial infarction (MI) one of the present compounds may be administered to a patient together with tPA to enhance the efficacy of the tPA treatment. As a further example, early re-occlusion following treatment of a patient with tPA may be prevented by the post-MI administration of one of the present compounds.

The compounds of formula (A) have been tested in a PAI functional assay. In this assay, a compound is incubated with PAI-1 prior to addition to the tPA assay system. Inhibition of PAI-1 results in the production of plasmin from plasminogen. In turn, plasmin cleaves the chromogenic substrate S2251 (Kabi Vitrum) producing pNA (p-nitroaniline) which is detected spectrophotometrically at 405 nm (K. Nilsson et al, Fibrinolysis (1987) 1, 163–168). The results of the assay are reported in Example 1 which follows.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 lo 10 mg/kg, most commonly in the range of 0.01 to 5 mg/kg, body weight. Such a dosage may be given, for example, from 1 to 5 times daily by bolus infusion, infusion over several hours and/or repeated administration. When one of the present compounds is administered in combination with tPA to adult humans, the dosage adopted for each route of administration is typically from 0.001 to 10 mg, more typically 0.01 to 5 mg per kg body weight for a compound of the invention and from 5 to 500 mg administered intravenously for the tPA. A suitable dosage regimen for the tPA is 100 mg given intravenously over 3 hours as follows: 10% of the total dose as an i.v. bolus over 1–2 minutes, 50% of the total dose as an infusion over 1 hour, 40% of the total dose as an infusion over the subsequent 2 hours.

A diketopiperazine of formula (A) or a pharmaceutically acceptable salt or ester thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use as an inhibitor of PAI comprising any one of the present compounds is therefore provided.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs, sweeteners; wetting agents such as lecithin, polysorbates, lauryl sulphates. Such preparations may be manufactured in known manners, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Some of the present compounds are insoluble in water. A compound may be encapsulated within liposomes.

The following Examples illustrate the invention:

EXAMPLE 1

Testing of the Present Compounds as PAI Inhibitors

Compounds of formula (A) were tested in a PAI chromogenic substrate assay. In the assay (K.Nilsson, Fibrinolysis (1987) 1, 163–168) each compound was incubated with PAI-1 prior to addition to the tPA assay system. Inhibition of PAI-1 by the compound of formula (Aa) resulted in the production of plasmin from plasminogen. In turn, the plasmin cleaved the chromogenic substrate S2251 (Kabi-Vitrum) producing pNA (p-nitroaniline) which was detected spectrophotometrically at 405 nm.

The degrees of inhibition observed in the chromogenic substrate assay at various concentrations of compounds of formula (A), or the $IC_{50}$ values, are presented in Table 1.

TABLE 1

| Compound | Concentration in $\mu M$ | | | | |
| --- | --- | --- | --- | --- | --- |
| No. | 100 | 50 | 25 | 12.5 | 6.25 |
| 1852 | 72 | 71 | 74 | 67 | 4 |
| 1920 | 68 | 66 | 57 | 50 | 33 |
| 1954 | 16 | 43 | 67 | 57 | 37 |
| 1955 | 9 | 2 | 3 | 2 | 0 |
| 1956 | 61 | 69 | 69 | 65 | 31 |
| 1957 | 10 | 1 | 2 | 1 | 1 |
| 1960 | 32 | 64 | 67 | 63 | 56 |
| 1962 | 2 | 2 | 1 | 1 | 1 |
| 1969 | 52 | 20 | 6 | 0 | 2 |
| 1978 | 50 | 41 | 11 | 0 | 3 |
| 1981 | 51 | 41 | 26 | 7 | — |
| 1885 | 54 | 31 | 2 | 0 | 0 |
| 1887 | 83 | 46 | 24 | 5 | 0 |
| 1889 | 49 | 38 | 15 | 3 | 0 |
| 1907 | 80 | 69 | 37 | 23 | 10 |
| 1908 | 74 | 69 | 66 | 29 | 12 |
| 1909 | 17 | 31 | 53 | 57 | 39 |
| 1911 | 38 | 23 | 15 | 20 | 13 |
| 1913 | 71 | 54 | 19 | 14 | 15 |
| 1924 | 64 | 38 | 18 | 7 | 9 |
| 1946 | 7 | 1 | 1 | 1 | — |
| 1947 | 1 | 1 | 1 | 1 | 0 |
| 1949 | 3 | 1 | 1 | 1 | 1 |

TABLE 1-continued

| | | | | | |
|---|---|---|---|---|---|
| 1951 | 43 | 23 | 2 | 1 | 0 |
| 1952 | 63 | 37 | 19 | 1 | 0 |
| 1953 | 0 | 0 | 1 | 1 | 1 |
| 1977 | 54 | 47 | 47 | 20 | 0 |
| 1979 | 37 | 0 | 0 | 0 | 0 |
| 1980 | 66 | 41 | 51 | 13 | 0 |
| 1984 | 17 | 0 | 0 | 0 | — |

| Compound | Concentration in μM | | | | |
|---|---|---|---|---|---|
| No. | 60 | 30 | 15 | 7.5 | 3.75 |
| 1914 | 27 | 17 | 15 | 15 | 20 |
| 1961 | 48 | 49 | 41 | 11 | 1 |

| Compound | Concentration in μM | | | |
|---|---|---|---|---|
| No. | 100 μM | 50 μM | 20 μM | $IC_{50}$ |
| 5058 | 67 | 68 | 75 | 6.0–3.0 |
| 5060.HCl | 75 | 65 | 52 | 25.0–12.0 |
| 5065.HCl | 85 | 80 | 12 | 50.0–20.0 |
| 5068.HCl | 75 | 76 | 81 | 12.0–6.0 |
| 5070.HCl | 40 | 6 | 6 | |
| 5080.HCl | 62 | 48 | 10 | 50.0–25.0 |
| 5186 | 46 | | 10 | |
| 5187 | 58 | | 10 | 100.0 |
| 5201 | 47 | | 43 | 2.50 |
| 5208 | 32 | | 10 | |
| 5209 | | | | 1.40 |
| 5210 | | | | 67.0 |
| 5228 | | | | 1.10 |
| 5229 | | | | 3.70 |
| 5230 | 9 | | 30 | 0.75 |
| 5231 | 36 | | 42 | 1.50 |
| 5232 | 10 | | | |
| 5233 | 50 | | 47 | 2.50 |
| 5234 | 10 | | | |
| 5235 | | | | 6.0 |
| 5236 | | | | 2.80 |
| 5237 | 67 | | 72 | 4.0 |
| 5238 | 36 | | 3 | |
| 5239 | 68 | | 65 | 7.0 |
| 5240 | 46 | | 65 | 6.50 |
| 5241 | 21 | | 1 | |
| 5245 | | | | 1.80 |
| 5246 | | | 34 | |
| 5248 | 10 | | | |
| 5249 | 55 | | 10 | |
| 5250 | 25 | | 10 | 14.0 |
| 5251 | 71 | | | 67.0 |
| 5254 | 79 | | 76 | 35.0 |
| 5255 | 33 | | 80 | 15.0 |
| 5256 | 65 | | 10 | 100.0 |
| 5259 | 10 | | 10 | |
| 5260 | | | | 17.0 |
| 5343 | | | 20 | |
| 5344 | | | 40 | |
| 5345 | | | 39 | |
| 5346 | | | 15 | |
| 5347 | | | 39 | |
| 5348 | | | 15 | |
| 5360 | | | 59 | 3.50 |
| 5365 | | | | 6.50 |
| 5365.HCl | | | | 3.30 |
| 5372 | | | | 11.0 |
| 5373 | | | | 13.0 |
| 5374 | | | | 15.0 |
| 5375 | | | | 4.50 |
| 5378 | | | 50 | 20.0 |
| 5380 | | | | 15.0 |
| 5381 | | | | 15.0 |
| 5385 | | | | 2.0 |
| 5398 | | | 54 | 4.20 |
| 5401 | | | 42 | |

EXAMPLE 2

Pharmaceutical Composition

Tablets, each weighing 0.15 g and containing 25 mg of a compound of the invention can be manufactured as follows:
Composition for 10,000 tablets
compound of the invention (250 g)
lactose (800 g)
corn starch (415 g)
talc powder (30 g)
magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

Reference Example 1

Preparation of (3Z,6Z)-3-benzvyidene-6-(4-methoxybenzylidene)-2,5-piperazinedione (3)

(Scheme 1)

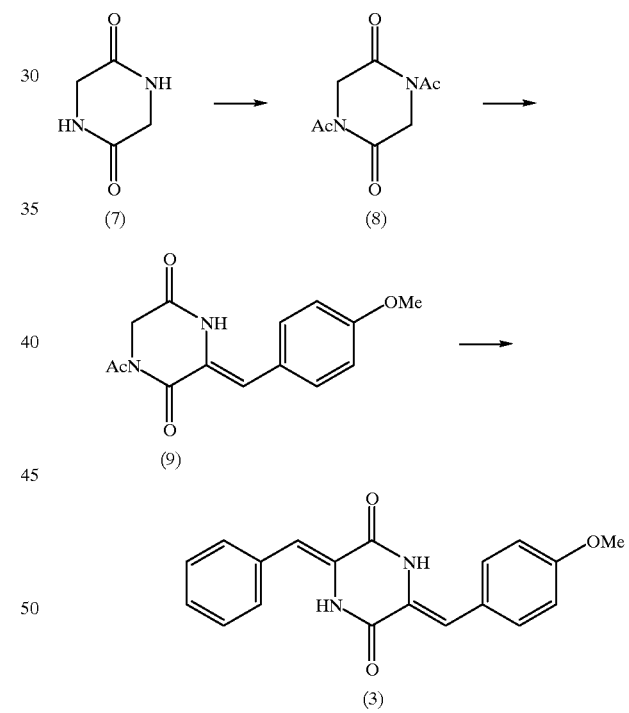

1,4-Diacetyl-2,5-piperazinedione (8)

1,4-Diacetylpiperazine-2,5-dione (8) was prepared by the published procedure (S. M. Marcuccio and J. A. Elix, *Aust. J. Chem.*, 1984, 37, 1791).

(3Z)-1-Acetyl-3-(4-methoxybenzylidene)-2,5-piperazinedione (9)

(3Z)-1-Acetyl-3-(4-methoxybenzylidene)-2,5-piperazinedione (9) was prepared by the published procedure (T. Yokoi, L-M. Yang, T. Yokoi, R-Y. Wu, and K-H. Lee, *J. Antibiot.*, 1988, 41, 494).

(3Z,6Z)-3-Benzylidene-6-(4-methoxybenzylidene)-2,5-piperazinedione (3)

A mixture of (3Z)-1-acetyl-3-(4-methoxybenzylidene)-2,5-piperazinedione (9) (1.0 g, 3.6 mmol), benzaldehyde (430 μl, 4.2 mmol) and triethylamine (1.14 ml), 8.2 mmol), in dry DMF (20 ml), was heated at 130° C. for 18 h. The reaction mixture was cooled to room temperature and poured into ethyl acetate (100 ml). A yellow solid precipitated which was filtered off and dried. Yield 360 mg (31%). $C_{19}H_{16}N_2O_3$ $^1$H nmr (400 MHz $d_6$-DMSO): δ: 3.80 (3H, s, o-Me); 6.77 (1H, s, CH=C); 6.78 (1H, s, CH=C); 6.98 (2H, d, J=8 Hz, 2×C-H on Ar-OMe); 7.30–7.56 (7H, m, Ph and 2×C-H on Ar-OMe); 10.15 (2H, br.s, N-H).

$^{13}$C nmr (100 MHz $d_6$-DMSO); δ: 58.68; 117.66; 118.03; 118.77; 128.11; 128.92; 129.95; 131.53; 132.11; 132.69; 134.44; 136.59; 161.39; 161.62; 162.71. ms (desorption chemical ionisation, ammonia): m/z (% relative intensity): 321 (100) MH$^+$. ir: KBr (diffuse reflectance): max (cm$^{-1}$): 1620, 1700, 3100, 3220. Elemental analysis: Calculated for $C_{19}H_{16}N_2O_3$: C 71.24, H 5.03, N 8.74. Found: C 70.92, H 5.02, N 8.80. C 70.89, H 5.06, N 8.79

Reference Example 2

Preparation of (3Z,6Z)-3-benzylidene-6-(4-methoxybenzylidene)-1-methyl-2,5-piperazinedione (1)

(Scheme 2)

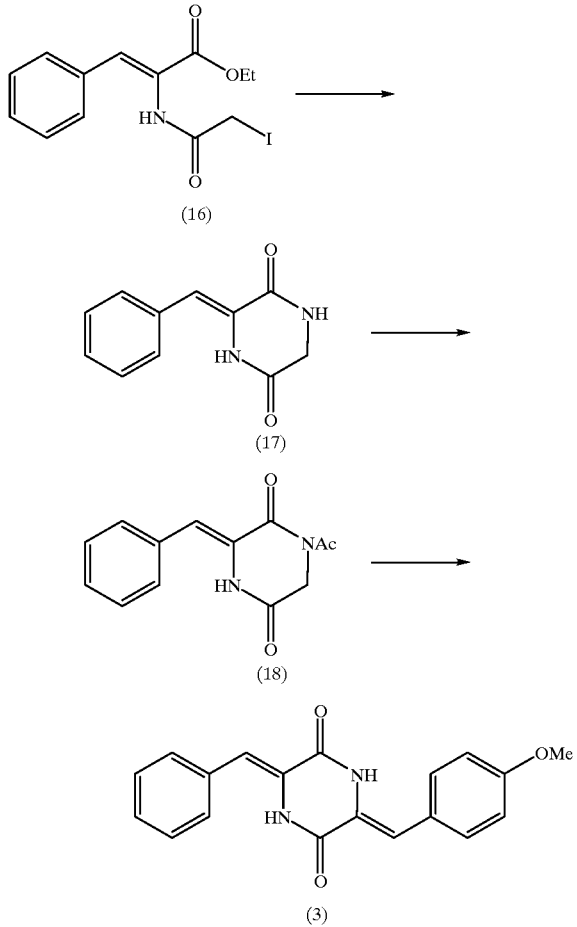

Compound 16 is treated with ammonia and subsequently with acetic anhydride to yield 1-acetyl-3-benzylidenepiperazine-2,5-dione (18).

Compound 18 is then condensed, in the presence of caesium carbonate or triethylamine in DMF, with 4-methoxybenzaldehyde to yield compound 3.

Reference Example 3

Preparation of 1-acetyl-3-benzylidene-2,5-piperazinedione 1,4-Diacetyl-2,5-piperazinedione (25.0 g, 126 mmol), which is compound (8) mentioned in Reference Example 1 was heated at 120–130° C. in DMF (200 ml) with triethylamine (17.6 ml, 126 mmol) and benzaldehyde (13.0 ml, 126 mmol). After 4 h the mixture was cooled to room temperature and poured into EtOAc (1000 ml), and washed three times with brine. Any solid formed at this stage was filtered off. The filtrate was dried (MgSO$_4$) and the solvent removed in vacuo. The residue was recrystallised from EtOAc:Hexane to give 11.78 g (38%) of the title compound as a yellow solid.

$^1$H NMR (CDCl$_3$ 400 MHz) δ=2.69 (3H, s) 4.54 (2H, s) 7.20 (1H, s) 7.40 (3H, m), 7.48 (2H, m), 7.93 (1H, br.s); MS(DCI,NH$_3$): 262 (MNH$_4^+$, 20%), 245 (MH$^+$, 53%), 220 (52%), 204 (100%), 203 (100%)

| Microanalysis | C | H | N |
|---|---|---|---|
| Calc | 63.93 | 4.95 | 41.47 |
| Found | 64.11 | 5.02 | 11.41 |
|  | 64.05 | 4.90 | 11.44 |

EXAMPLE 3

Preparation of compound 1908

1-Acetyl-3-benzylidene-2,5-piperazinedione (one equivalent), prepared according to Reference Example 2, was treated with 4-(3-dimethylaminopropoxy)benzaldehyde in the presence of Cs$_2$CO$_3$ (1-1.1 equivalents) in DMF at 80–100° C. for 1–8 hours. The title compound was obtained in 51% yield.

By the same method, but replacing 4-(3-dimethylaminopropoxy)benzaldehyde by the appropriately substituted benzaldehyde, the following compounds were prepared:

| Compound | Yield (%) | Compound | Yield (%) |
|---|---|---|---|
| 1889 | 41 | 1950 | 24 |
| 1913 | 37 | 1951 | 49 |
| 1924 | 44 | 1953 | 9 |
| 1946 | 32 | 1984 | 15 |
| 1949 | 33.5 |  |  |

Characterising data for the compounds are set out in Example 14.

Reference Example 4

Preparation of (3Z,6Z)-3-(4-hydroxybenzylidene)-6-(4-methoxybenzylidiene)-2,5-piperazinedione (3Z)-1-Acetyl-3-(4-methoxybenzylidene)-2,5-piperazinedione (1 equivalent), which is compound (9) mentioned in Reference Example 1, was treated with 4-acetoxybenzaldehyde (1 equivalent) in the presence of Cs$_2$CO$_3$ (1 to 1.1 equivalents) in DMF at 80 to 100° C. for 1 to 6 hours. The compound (3Z,6Z)-3-(4-acetoxybenzylidene)-6-(4-methoxybenzylodiene)-2,5-piperazinedione was obtained in 21% yield. That compound was then treated with aqueous sodium hydroxide in THF at room temperature for 8 hours to give (3Z,6Z)-3-(4-hydroxybenzylidene)-6-(4-methoxybenzyladine)-2,5-piperazinedione (compound 1519) in 30% yield.

EXAMPLE 4

Preparation of Compounds 1885, 1887 and 1909

Compound 1519, prepared as described in Reference Example 4, was treated with $(CH_3)_3CCH_2C(O)Cl$ (1 equivalent) in DMF in the presence of sodium hydride (2 equivalents) at room temperature for 4 hours. Compound 1885 was obtained in 29% yield.

Under the same conditions, but replacing the acid chloride by $CH_3(CH_2)_5COCl$ (1 equivalent) compound 1887 was obtained in 83% yield.

Under conditions analogous to those used in Reference Example 4, but using the appropriately substituted benzaldehyde and heating at 80° C. for five hours, Compound 1909 was obtained.

EXAMPLE 5

Preparation of Compound 36 and 1947

1,4-Diacetyl-2,5-piperazinedione, Compound (8) mentioned in Reference Example 1, was treated with 4-(3-dimethylaminopropoxy)benzaldehyde (2 equivalents) in DMF in the presence of $Cs_2CO_3$ (2.1 equivalents) at 90° C. for two hours. Compound 36 was obtained in 50% yield.

Under the same conditions, but using 4-(2-dimethylaminoethoxy)benzaldehyde, Compound 1947 was obtained in 30% yield.

EXAMPLE 6

Preparation of Compounds 1907 and 1911

Compound (9), prepared as described in Reference Example 1, was treated with 4-n-hexyloxybenzaldehyde in DMF in the presence of $Cs_2CO_3$ at 90° C. for two hours. Compound 1907 was obtained in 78% yield.

Under analogous conditions, but replacing the substituted benzaldehyde by 4-(2-dimethylaminoethoxy)benzaldehyde and heating at 80° C. for four hours, Compound 1911 was obtained in 39% yield.

EXAMPLE 7

Preparation of Compound 1952

1,4-Diacetyl-2,5-piperazinedione, Compound (8) mentioned in Reference Example 1, was treated with 2,5-dichlorobenzaldehyde in DMF in the presence of triethylamine to give 1-acetyl-(2,6-dichlorobenzyladiene)-2,5-piperazinedione. This was treated with 4-(2-dimethylaminoethoxy)benzaldehyde in DMF in the presence of $Cs_2CO_3$ for two hours to give Compound 1952 in 59% yield.

Reference Example 5

Preparation of (3Z)-1-acetyl-3-(4-(3-dimethylamino)propoxybenzylidene)-2,5-piperazinedione 1,4-Diacetyl-2,5-piperazinedione, which is compound 8 described in Reference Example 1, was stirred in DMF with 4-(3-dimethylamino)propoxybenzaldehyde and triethylamine and heated to 120° C.–130° C. for 2–4 hours, to yield the title compound.

EXAMPLE 8

Preparation of 5186

(3Z)-1-acetyl-3-(4-(3-dimethylamino)propoxy)-benzylidene-2,5-piperazinedione, prepared as in Reference Example 5, was treated with 2-methylbenzaldehydre in DMF in the presence of $Cs_2CO_3$ at 80–90° C. for 2–4 hours. Compound 5186 was obtained in 47% yield.

By the same method, but replacing 2-methylbenzaldehyde by the appropriately substituted benzaldehyde, the following compounds were prepared:

| Compound | Yield (%) | Compound | Yield (%) |
|---|---|---|---|
| 5060 | 41 | 5246 | 51 |
| 5068 | 48 | 5247 | 50 |
| 5187 | 61 | 5248 | 31 |
| 5201 | 41 | 5251 | 62 |
| 5229 | 45 | 5252 | 63 |
| 5208 | 55 | 5255 | 20 |
| 5209 | 55 | 5343 | 49 |
| 5228 | 44 | 5344 | 22 |
| 5232 | 63 | 5345 | 68 |
| 5233 | 45 | 5346 | 46 |
| 5234 | 70 | 5347 | 59 |
| 5235 | 78 | 5348 | 46 |
| 5236 | 82 | 5360 | 73 |
| 5237 | 73 | 5365 | 76 |
| 5238 | 45 | 5366 | 89 |
| 5239 | 72 | 5373 | 59 |
| 5241 | 67 | 5374 | 46 |
| 5242 | 55 | 5398 | 28 |
| 5375 | 25 | 5401 | 53 |
| 5385 | 71 | | |

EXAMPLE 9

Preparation of 5249

(3Z)-1-acetyl-3-(2-chloro)benzylidene-2,5-piperazinedione was treated with 4-(3-dimethylamino)propoxybenzaldehyde, in DMF in the presence of $Cs_2CO_3$ at 80° C.–90° C. for 2–4 hours. Compound 5249 was obtained in 68% yield.

By the same method, but using a corresponding piperazinedione derivative in which the 2-chloro substituent on the phenyl group of the benzylidene moiety was replaced by the substituents shown below, the following compounds of formula (I) were prepared:

| Substitution on phenyl group | Compound of formula (I) | Yield (%) |
|---|---|---|
| 4-n-butoxy | 5250 | 58 |
| 3,5-dichloro | 5372 | 58 |
| 3,5-dinitro | 5378 | 72 |

By the same method but using (3Z)-1-acetyl-3-benzylidene-2,5-piperazinedione, prepared as in Reference Example 3, and 4-(2-diethylamino)ethoxybenzaldehyde the compound 5065 was prepared in 45% yield.

EXAMPLE 10

Preparation of compounds of formula (I)

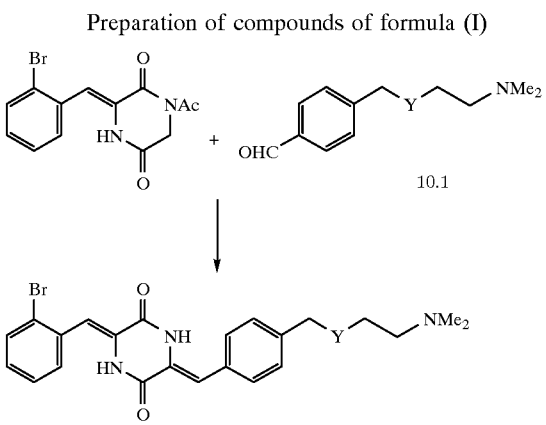

(3Z)-1-acetyl-3-(2-bromo)benzylidene was treated with the benzaldehyde derivative 10.1 in which Y was O or S, in DMF in the presence of $Cs_2CO_3$ at 80° C.–90° C. for 2–4 hours, to give compounds 5070 and 5080, respectively, in respective yields of 15% and 28%.

EXAMPLE 11

Preparation of Salts

1. Compound 1981, the salt with hydrochloric acid of Compound 1953, was prepared by bubbling HCl gas through a solution of Compound 1953 (the corresponding free base) in THF at room temperature, followed by evaporation to dryness and recrystallization. The salt was obtained in 66% yield.

By the same procedure, the following salts were prepared:

| No of Compounds of Formula (I) | No of Salt | Yield (%) |
|---|---|---|
| 1913 | 1914 | |
| 1951 | 1960 | |
| 1984 | 1969 | |
| 1949 | 1978 | |
| 1946 | 1979 | |
| 1952 | 1980 | |
| 5060 | 5060.HCl | 99 |
| 5068 | 5068.HCl | 50 |
| 5186 | 5204 | 32 |
| 5187 | 5203 | 42 |
| 5201 | 5229 | 45 |
| 5208 | 5210 | 27 |
| 5209 | 5231 | 57 |
| 5237 | 5240 | 64 |
| 5246 | 5254 | 18 |
| 5247 | 5256 | 30 |
| 5248 | 5259 | 71 |
| 5360 | 5360.HCl | 19 |
| 5365 | 5365.HCl | 46 |
| 5401 | 5401.HCl | 81 |
| 5249 | 5084 | |
| 5372 | 5380 | 86 |
| 5378 | 5381 | 63 |
| 5065 | 5065.HCl | 83 |
| 5080 | 5080.HCl | 97 |
| 5070 | 5070.HCl | 31 |
| 5058 | 5058.HCl | 28 |

2. By bubbling HCl gas through a solution of the free base in hot DMF, the following hydrochloride salts of compounds of formula (I) were prepared:

| No of Compounds of Formula (I) | No of Salt | Yield (%) |
|---|---|---|
| 5228 | 5230 | 67 |
| 5248 | 5245 | 46 |
| 5385 | 5385.HCl | 95 |
| 5398 | 5398.HCl | 65 |

EXAMPLE 12

Preparation of Compound 1977

1-Acetyl-3-(2,4-difluorobenzylidene)-2,5-piperazinedione was prepared by a process analogous to that described in Reference Example 3, but replacing benzaldehyde by 2,4-difluorobenzaldehyde. That compound was treated with 4-(3-dimethylaminopropoxy)benzaldehyde in the presence of $Cs_2CO_3$ (1 to 1.1 equivalents) in DMF at 80 to 100° C. for 1 to 8 hours to yield Compound 1977. Compound 1977 was converted to its salt by the method described in Example 11.

EXAMPLE 13

Preparation of 5260

Compound 5260 was prepared by treating the corresponding phthalimide derivative with hydrazine in $H_2O$ and THF at room temperature for 5 hours.

EXAMPLE 14

Characterization of the Present Compounds

The compounds and salts of the invention were characterised by conventional mass spectroscopic, nmr and microanalytical techniques. The resulting data are set out in the following Tables:

| No. | Mol. Formula (M. Wt) | Mass spec m/z. mass intensity (mode) | $^1$H nmr Solvent δ all 400 MHz | Microanalysis Calc | Found |
|---|---|---|---|---|---|
| XR1920 | $C_{27}H_{34}O_4N_3Cl$ 499.5 | 464, 99%. $C2^+$ | $D_4$–MeOH 400 MHz 1.1 (3H, t); 1.6 (2H, m); 2.1 (2H, m); 2.3 (2H, m); 3.0 (6H, s); 3.5 (2H, m); 4.1 (2H, t); 4.3 (2H, t); 4.9 (methanol); 7.0 (2H, 2×s); 7.1 (2H, d); 7.15 (2H, d); 7.4 (4H, t). | | |

-continued

| | | | | | | | |
|---|---|---|---|---|---|---|---|
| XR1914 | $C_{21}H_{22}N_3O_2Cl$ | 348 (M±Cl) 100% | DMSO 2.72 (6H, s, NMe$_2$); 4.25 (2H, s, CH$_2$N); 6.80 (2H, s); 7.32–7.62 (9H, m, Ar); 9.95 (1H, br.s, NH); 10.25 (2H, br.s, 2×NH). | | | | |
| XR1913 | $C_{21}H_{21}N_3O_2$ 347 | 347 (M+, 30%), 303 (M+–NMe$_2$, 80%), 130 (75%); 58 (100%, possibly CH$_2$NMe$_2$). EI | DMSO 2.15 (6H, s, 2×Me); 3.40 (2H, s, CH$_2$Ar); 6.75 (2H, s); 7.35–7.55 (9H, m, aryl CH); 10.20 (2H, br.s, 2×NH). | | | | |
| XR1911 | $C_{23}H_{25}N_3O_4$ 407 | 408 (MH+, 12%), 350 (MH+–CH$_2$NMe$_2$, 10%), 58 (100%). EI | CDCl$_3$/TFA 3.08 (6H, s, NMe$_2$); 3.64–3.67 (2H, m); 3.88 (3H, s, OMe); 4.38–4.44 (2H, m); 6.95–7.45 (10H, m, aryl CH). | | | | |
| XR1909 | $C_{26}H_{27}N_3O_6$ 477 | 495 (M$^+$+NH$_4$, 13%); 478 (M$^+$+1, 100%); 446 (M$^+$– OMe, 15%). EI | CDCl$_3$+TFA 2.00–2.17 (2H, m); 2.45–2.52 (4H, m); 3.75 (3H, s, Me); 3.88 (3H, s, Me); 4.50 (2H, s); 7.00–7.40 (10H, m). | | | | |
| XR1908 | $C_{22}H_{23}N_3O_3$ 377 | 378 (M$^+$+1, 100%). EI | CDCl$_3$+TFA 3.10 (6H, s, 2×Me); 3.65 (2H, t, CH$_2$); 4.40 (2H, t, CH$_2$); 6.95–7.50 (11H, m). | | | | |
| XR1907 | $C_{25}H_{28}O_4N_2$ | 421 (98%) C2+ | CDCl$_3$ 400 MHz 0.90 (3H, t); 1.3 (4H, m); 1.5 (2H, m); 1.8 (2H, m); 3.9 (3H, s); 4.1 (2H, t); 7.0 (4H, d×d); 7.2 (4H, s); 7.25 (1H, s); 7.4 (4H, d×d); 10.1 (1H, s). | | | | |
| XR1889 | $C_{24}H_{24}N_2O_4$ | 405 (MH+, 23%); 306 (100%). DCl NH | CDCl$_3$/TFA 400 1.16 (9H, s); 2.51 (2H, s); 7.20 (2H, d, J=8 Hz); 7.23 (1H, s); 7.29 (1H, s); 7.40–7.54 (7H, m). | | | | |
| XR1887 | $C_{26}H_{28}N_2O_5$ 448 | 449 (MH+, 58%); 448 (50%); 336 (100%); 146 (43%). | CDCl$_3$/TFA 400 MHZ 0.95 (3H, t, J=6 HZ); 1.30–1.41 (4H, m); 1.41–1.52 (2H, m); 1.75–1.84 (2H, m); 2.65 (2H, t, J=6 Hz); 3.95 (3H, s); 7.05 (2H, d, J=8 Hz); 7.20–7.31 (4H, m); 7.46 (2H, d, J=8 Hz); 7.51 (2H, d, J=8 HZ). | | | | |
| XR1885 | $C_{25}H_{26}N_2O_5$ | | 400 MHZ CDCl$_3$ TFA 1.18 (9H, s); 4.54 (2H, s); 3.90 (3H, s); 7.01 (2H, d, J=8 Hz); 7.15–7.28 (4H, m); 7.40–7.49 (4H, m). | | | | |
| XR1852 | $C_{23}H_{26}N_3O_3Cl$ | 392 ([M–Cl]+, 100%). ESI | DMSO 400 MHz 2.15 (2H, m); 3.18 (2H, m); 3.25 (6H, s); 4.10 (2H, t, J=6 Hz); 6.75 (1H, s); 6.77 (1H, s); 7.00 (2H, d, J=8 Hz); 7.34 (1H, m); 7.42 (2H, m); 7.52–7.59 (4H, m). | | | 63.16 6.06 9.19 | |
| XR1955 | $C_{32}H_{42}N_4O_8 \cdot 2H_2O$ | | DMSO 400 MHz 1.87 (4H, m); 2.21 (12H, s); 2.39 (4H, s); 2.48 (4H, t, J=6 Hz); 4.06 (4H, t, J=6 Hz); 6.75 (2H, s); 7.00 (4H, d, J=8 Hz); 7.52 (4H, d, J=8 Hz). | C H N | 59.43 7.17 8.66 | 59.23 7.14 8.48 | 59.22 7.07 8.57 |
| XR1954 | $C_{26}H_{29}N_3O_7$ | | DMSO 400 MHz 2.29 (6H, s); 2.43 (4H, s); 2.72 (2H, t, J= 6 Hz); 4.10 (2H, t, J=6 Hz); 6.74 (1H, s); 6.75 (1H, s); 7.00 (2H, d, J=8 Hz); 7.31 (1H, m); 7.40 (2H, m); 7.46–7.58 (4H, m). | C H N | 63.02 5.90 8.48 | 62.75 5.81 8.50 | 63.02 5.87 8.49 |
| XR1953 | $C_{29}H_{39}N_5O_2$ 489 | 489 18% 403 24% 303 100% 186 62% 141 68% 85 97% 58 85% EI+ | CDCl$_3$ 400 MHz 1.66 (4H, OUI), 2.22 (12H, s), 2.28 (4H, t), 2.48 (2H, t), 3.60 (2H, s), 7.04 (2H, overlapping signals), 7.32–7.50 (9H, overlapping signals). | | | | |
| XR1952 | $C_{22}H_{21}N_3O_3Cl_2$ 446/447/449 9:6:1 | MH+ (20%) 445 9 447 6 449 1 Cl/NH$_3$ | CDCl$_3$, CF$_3$CO$_2$D 400 MHz 7.43 (m, 4H); 7.33 (m, 1H); 7.25 (s, 1H); 7.13 (s, 1H); 7.00 (d, 2H); 4.42 (t, 2H); 3.67 (t, 2H); 3.09 (s, 6H). | C H N | 59.20 4.74 9.41 | 58.97 4.73 9.23 | 58.96 4.72 9.24 |
| XR1951 | $C_{22}H_{22}N_3O_3Cl$ 411/413 (3:1) | MH+ (100%) 412 (35%) 414 378 (10%) Cl/NH$_3$ | CDCl$_3$ TFAA 7.51–7.41 (m, 5H), 7.36 (d, 1H), 7.22 (2×s, 2H), 7.07 (d, 1H), 6.90 (dd, 1H), 4.42 (t, 2H), 3.65 (t, 2H), 3.07 (s, 6H). | | | | |
| XR1949 | $C_{26}H_{32}N_4O_4$ 464 | MH+ (100%) 465 393 (70%) 349 (40%) 194 (20%) | CDCl$_3$ 400 MHz 8.11 (broad s, 2H), 7.47 (m, 2H), 7.40 (m, 3H), 7.05–6.90 (m, 5H), 4.14 (m (2 merged triplets), 4H), 2.79 (m (2 merged triplets), 4H), 2.38 (s, 12H). | | | | |

-continued

| | | | | | | | |
|---|---|---|---|---|---|---|---|
| XR1948 | $C_{26}H_{34}N_4O_4Cl_2$ 537 | MH+ (100%) 465 (free amine) | $D_2O$ 400 MHz 7.6–7.0 (m, 10H), 4.53 (m, 4H), 3.75 (t, 4H), 3.15 (s, 12H). | | | | |
| XR1947 | $C_{26}H_{32}N_4O_4$ 464 | MH+ (100%) 465 | $CDCl_3$ 400 MHz 8.18 (broad s, 2H), 7.35 (m, 2H), 7.0–6.9 (m, 8H), 4.11 (t, 4H), 2.78 (t, 4H), 2.38 (s, 12H). | | | | |
| XR1946 | $C_{22}H_{23}N_3O_3$ 377 | MH+ (100%) 378 | $CDCl_3$ 400 MHz 8.96 (broad, s, 1H), 8.10 (broad s, 1H), 7.47–7.32 (m, 7H), 7.06–7.01 (m, 4H), 4.24 (t, 2H), 2.85 (t, 2H), 2.35 (s, 6H). | | | | |
| XR1924 | $C_{22}H_{23}N_3O_3$ 377 | MH+ (100%) 378 CI/$NH_3$ | $CDCl_3$ 400 MHz 8.12 (br, 2×s, 2H), 7.50–7.35 (m, 7H), 7.05 (s, 1H), 7.0–6.95 (m, 3H), 4.11 (t, 2H), 2.78 (t, 2H), 2.85 (s, 6H). | | | | |
| XR1962 | $C_{26}H_{34}N_4O_4Cl_2$ | 233 (100%), 465 (10%), 929 (50%). | $CDCl_3$+TFA 3.05 (12H, s), 3.55 (4H, m), 4.45 (4H, m), 7.00 4H, d), 7.20 (2H, s), 7.42 (4H, d). | | | | |
| XR1961 | $C_{22}H_{24}N_3O_3Cl$ 413.5 | MH+ (100%) free amine 378 CI/$NH_3$ | $d_6$-DMSO 400 MHz 10.23 (br, 2H), 7.55–7.30 (m, 6H), 7.17 (m, 2H), 6.96 (m, 1H), 6.80 (s, 1H), 6.79 (s, 1H), 4.35 (t, 2H), 3.33 (broad t, 2H), 2.71 (s, 6H). | | | | |
| XR1960 | $C_{22}H_{23}N_3O_3Cl_2$ 448 | MH+ (100%) 412 (30%) 414 bath free amine | $d_6$-DMSO 10.30 (s, 1H); 10.23 (s, 1H); 10.10 (broad, s, 1H); 7.62 (d, 1H); 7.55 (d, 2H); 7.42 (m, 2H); 7.35 (m, 1H); 7.22 (d, 1H); 7.05 (dd, 1H); 6.81 (s, 1H); 6.80 (s, 1H); 4.41 (t, 2H); 3.52 (t, 2H); 2.84 (s, 6H). | | | | |
| XR1957 | $C_{30}H_{44}N_4O_{10}S_2$ | | $D_2O$ 400 MHz 2.26 (4H, m); 2.89 (6H, s); 2.99 (12H, s); 3.38 (4H, m); 4.24 (4H, m); 6.92 (2H, s); 7.18 (4H, d, J=8 Hz); 7.57 (4H, d, J=8 Hz). | | 52.62 6.48 8.18 | 52.69 6.46 8.13 | 52.70 6.47 8.13 |
| XR1956 | $C_{23}H_{27}N_3O_6S$ | | DMSO 400 MHz 2.33 (3H, s); 2.90 (6H, s); 3.55 (2H, J= 6 Hz); 4.34 (2H, t, J=6 Hz); 6.78 (2H, s); 7.08 (2H, d, J=8 Hz); 7.35 (1H, m); 7.42 (2H, m); 7.53–7.62 (4H, m). | | | | |
| XR1984 | $C_{26}H_{32}N_4O_4$ 464 | MH+ (100%) 465 (20%) 393 CI/$NH_3$ | $CDCl_3$ 400 MHz 9.07 (s, br, 1H), 8.08 (s, br, 1H), 7.48–7.35 (m, 5H), 7.25 (d, 1H), 6.98 (s, 1H), 6.96 (s, 1H), 6.60 (m, 2H). | | | | |
| XR1981 | $C_{29}H_{39}N_5O_2$.3HCl 489+106.5 | 526 7% (MHCl) 490 4% (MH+) 266 100% | DMSO $d_6$ 400 MHz 2.28 (4H, V. BROAD SIGNAL), 2.78 (12H, s), 3.15 (8H, V. BROAD SIGNAL(s)), 4.40 (2H, BROAD PEAK), 6.82 (2H, OVERLAPPING SIGNALS), 7.36 (2H, BROAD SIGNAL), 7.44 (2H, t), 7.56 (2H, d), 7.64 (2H, BROAD SIGNAL), 7.75 (1H, BROAD SIGNAL). | | | | |
| XR1980 | $C_{22}H_{22}N_3O_3Cl_3$ 482.5 | MH+ (100%) 446, (60%) 448, (10%) 450, all free amine; 412 (30%). | $d_6$-DMSO 400 MHz 10.47 (s, 1H); 10.25 (s, 1H); 10.10 (br, s, 1H); 7.54 (d, 2H); 7.49 (d, 2H); 7.38 (d, 1H); 7.06 (d, 2H); 6.79 (s, 1H); 6.58 (s, 1H); 4.38 (t, 2H); 3.48 (t, 2H); 2.83 (s, 6H). | C H N Cl | 54.73 4.59 8.70 22.05 | 54.43 4.67 8.56 21.40 | 54.20 4.63 8.51 |
| XR1979 | $C_{22}H_{24}N_3O_3Cl$ 413.5 | | $d_6$-DMSO 10.18 (s, 1H); 10.02 (s, 1H); 9.83 (br, s, 1H); 7.55–7.32 (m, 7H); 7.12 (d, 1H); 7.06 (m, 1H); 6.86 (s, 1H); 6.78 (s, 1H); 4.39 (t, 2H); 3.50 (br, 2H); 2.81 (s, 6H). | | | | |
| XR1978 | $C_{26}H_{34}N_4O_4Cl_2$ 537 | MH+ (45%) 465 free amine 393 (30%), 349 (20%), 219 (100%). | $D_2O$ 400 MHz 7.56 (m, 2H); 7.32 (m, 1H); 7.25–7.20 (m, 4H); 7.05 (s, 2H), 4.52 (t, 4H); 3.72 (t, 4H); 3.06 (s, 12H). | | | | |
| XR1977 | $C_{22}H_{21}N_3O_3F_2$ 413 | MH+ 414 (100%) DCI, $NH_3$ | $CDCl_3$+TFA 3.08 (6H, s); 3.12 (2H, m); 4.40 (sH, m); 6.97 (4H, m); 7.15 (1H, s); 7.25 (1H, s); 7.45 (3H, m). | | | | |
| XR1969 | $C_{26}H_{34}N_4O_4Cl_2$ 537 | MH+ (100%) 465 free amine 393 (15%); 270 (30%). CI/$NH_3$ | $D_2O$ 400 $MH_z$ 7.65–7.52 (m, 6H); 7.07 (m, 2H); 6.92 (d, 1H); 6.82 (s, 1H); 4.50 (m, 4H); 3.74 (br, 2H); 3.68 (br, 2H); 3.07 (s, 12H). | | | | |
| XR1634 | $C_{20}H_{16}N_2O_4$ 348 | 366 ($M^+NH_4$, 20%), 349 ($M^+OH$, 72%), 317 (100%). CI | $CDCl_3$-TFA 400 MHz 3.94 (3H, s); 7.17 (1H, s); 7.23 (1H, s); 7.31–7.55 (8H, m); 8.03 (1H, d). | | | | |

-continued

| No. | Mol. Formula | Mass spec. data mass (intensity) | mode | $^1$H nmr data solvent (field) | δ |
|---|---|---|---|---|---|
| 5210 | $C_{23}H_{24}N_4O_5 \cdot HCl$ | 437 (100) | CI | $d_6$-DMSO/400 MHz | 2.15–2.20 (2H, m), 2.80 (6H, m), 3.19–3.26 (2H, m), 4.11 (2H, t), 6.78 (1H, s), 6.98 (1H, s), 7.01 (2H, d), 7.55 (2H, d), 7.58–7.69 (2H, m), 7.76–7.81 (1H, m), 8.15 (1H, d), 10.25 (1H, brs), 10.39 (1H, brs), 10.44 (1H, brs). |
| 5060 | $C_{23}H_{24}BrN_3O_3 \cdot HCl$ | 472 (100), 470 (100). | EI | $d_6$-DMSO/400 MHz | 2.16 (2H, m), 2.76 (6H, d), 3.20 (2H, m), 4.10 (2H, t), 6.73 (1H, s), 6.77 (1H, s), 7.01 (2H, d), 7.26 (1H, m), 7.43 (1H, m), 7.53 (2H, d), 7.59 (1H, m), 7.70 (1H, d), 10.30 (1H, brs), 10.38 (1H, brs), 10.65 (1H, brs). |
| 5065 | $C_{24}H_{27}N_3O_3$ | 406 (10) | CI | $CDCl_3+CF_3CO_2D$/400 MHz | 1.42 (6H, t), 3.34–3.50 (4H, m), 3.65 (2H, t), 4.37 (2H, t), 6.95 (2H, d), 7.24 (1H, s), 7.26 (1H, s), 7.40–7.52 (7H, m). |
| 5068 | $C_{25}H_{30}N_4O_3 \cdot HCl$ | | | $CDCl_3$/400 MHz | 2.35 (2H, m), 2.98 (6H, s), 3.27 (6H, s), 3.40 (2H, m), 4.14 (2H, t), 6.96 (1H, s), 6.99 (1H, s), 7.18 (2H, d), 7.40 (2H, d), 7.59 (2H, d), 7.75 (2H, d). |
| 5070 | $C_{23}H_{24}BrN_3O_3 \cdot HCl$ | 472 (25), 470 (25). | CI | $d_6$-DMSO/400 MHz | 2.79 (6H, s), 3.35 (2H, t), 3.80 (2H, t), 4.57 (2H, s), 6.79 (1H, s), 6.81 (1H, s), 7.28 (1H, m), 7.40–7.45 (3H, m), 7.55–7.60 (3H, m), 7.70 (1H, m), 9.82 (1H, s), 10.31 (1H, s), 10.43 (1H, s). |
| 5058 | $C_{23}H_{25}N_3O_2S$ | 408 (10) | CI | $CDCl_3$/400 MHz | 2.32 (6H, s), 2.50 (4H, brs), 3.75 (2H, s), 7.00 (1H, s), 7.02 (1H, s), 7.35–7.50 (9H, m), 8.10 (2H, brs). |
| 5080 | $C_{23}H_{24}BrN_3O_2S \cdot Hcl$ | | | $d_6$-DMSO/400 MHz | 2.74 (6H, s), 2.80 (2H, m), 3.26 (2H, m), 3.87 (2H, s), 6.76 (1H, s), 6.79 (1H, s), 7.28 (1H, m), 7.44 (2H, d), 7.49 (1H, m), 7.55 (2H, d), 7.60 (1H, d), 7.74 (1H, d), 10.32 (1H, brs), 10.44 (1H, brs), 10.49 (1H, brs). |
| 5084 | $C_{23}H_{24}N_3O_2 \cdot HCl$ | | | $d_6$-DMSO/400 MHz | 2.16 (2H, m), 2.80 (6H, m), 3.22 (2H, m), 4.12 (2H, t), 6.79 (1H, s), 6.81 (1H, s), 7.02 (2H, d), 7.40 (2H, m), 7.55 (3H, m), 7.62 (1H, m). |
| 5186 | $C_{24}H_{27}N_3O_3$ | 406 (100) | ESI | $d_6$-DMSO/400 MHz | 1.8–1.9 (2H, m), 2.17 (6H, s), 2.29 (3H, s), 2.38 (2H, t), 4.05 (2H, t), 6.72 (1H, s), 6.79 (1H, s), 6.99 (2H, d), 7.22–7.31 (3H, m), 7.40–7.45 (1H, m), 7.52 (2H, d), 9.90 (1H, brs), 10.28 (1H, brs). |
| 5187 | $C_{24}H_{27}N_3O_3$ | 406 (100) | ESI | $d_6$-DMSO/400 MHz | 1.81–1.90 (2H, m), 2.12 (6H, s), 2.34–2.40 (5H, m), 4.08 (2H, t), 6.75 (2×1H, s), 6.99 (2H, d), 7.12–7.18 (1H, m), 7.30–7.35 (2H, m), 7.39 (1H, brs), 7.51 (2H, d), 9.9 (1H, brs), 10.18 (H, brs). |
| 5201 | $C_{24}H_{25}N_3O_5$ | 436 (100) | ESI | $d_6$-DMSO/400 MHz | 1.82–1.89 (2H, m), 2.15 (6H, s), 2.35 (2H, t), 4.1 (2H, t), 6.09 (2H, s), 6.7 (2H, d), 6.95–7.0 (3H, m), 7.01–7.08 (1H, m), 7.18 (1H, s), 7.5 (2H, d), 10.12 (2H, brs). |
| 5203 | $C_{24}H_{27}N_3O_3 \cdot HCl$ | 406 (100) | ESI | $d_6$-DMSO/400 MHz | 2.12–2.21 (2H, m), 2.35 (3H, s), 2.77 (6H, s), 3.19–3.23 (2H, m), 4.11 (2H, t), 6.71 (1H, s), 6.73 (1H, s), 7.01 (2H, d), 7.11–7.15 (1H, m), 7.29–7.32 (2H, m), 7.39 (1H, s), 7.52 (2H, d), 10.15 (2H, d), 10.60 (1H, brs). |
| 5204 | $C_{24}H_{27}N_3O_3 \cdot HCl$ | 406 (100) | ESI | $d_6$-DMSO/400 MHz | 2.12–2.21 (2H, m), 2.28 (3H, s), 2.78 (6H, s), 3.19–3.23 (2H, m), 4.11 (2H, t), 6.76 (1H, s), 6.81 (1H, s), 7.0 (2H, d), 7.23–7.29 (3H, m), 7.40–7.45 (1H, m), 7.54 (2H, d), 9.4 (1H, brs), 10.19 (1H, brs), 10.50 (1H, brs). |
| 5208 | $C_{23}H_{24}N_4O_5$ | 437 (100) | CI | $d_6$-DMSO/400 MHz | 1.81–1.90 (2H, m), 2.18 (6H, s), 2.38 (2H, t), 4.05 (2H, t), 6.75 (1H, s), 6.98 (1H, s), 7.00 (2H, d), 7.50 (2H, d), 7.61 (1H, d), 7.69 (1H, d), 7.79 (1H, t), 8.15 (1H, d), 10.35 (2H, brs). |
| 5210 | $C_{23}H_{24}N_4O_5 \cdot HCl$ | 437 (100) | CI | $d_6$-DMSO/400 MHz | 2.15–2.20 (2H, m), 2.80 (6H, s), 3.19–3.26 (2H, m), 4.11 (2H, t), 6.78 (1H, s), 6.98 (1H, s), 7.01 (2H, d), 7.55 (2H, d), 7.58–7.69 (2H, m), 7.76–7.81 (1H, m), 8.15 (1H, d), 10.25 (1H, brs), 10.39 (1H, brs), 10.44 (1H, brs). |
| 5229 | $C_{24}H_{25}N_3O_5 \cdot HCl$ | 436 (40) | CI | $d_6$-DMSO/400 MHz | 2.12–2.19 (2H, m), 2.75 (6H, s), 3.15–3.20 (2H, m), 4.10 (2H, t), 6.08 (2H, s), 6.70 (1H, s), 6.72 (1H, s), 6.95–7.09 (4H, m), 7.16 (1H, s), 7.51 (2H, d), 10.11 (1H, brs), 10.18 (1H, brs). |
| 5230 | $C_{23}H_{24}N_4O_5 \cdot HCl$ | 473 (100) | CI | $d_6$-DMSO/400 MHz | 2.10–2.19 (2H, m), 2.78 (6H, s), 3.10–3.22 (2H, m), 4.11 (2H, t), 6.78 (1H, s), 6.80 (1H, |

-continued

| | | | | | |
|---|---|---|---|---|---|
| | | | | | s), 7.0 (2H, d), 7.55 (2H, d), 7.79 (2H, d), 8.22 (2H, d), 10.28 (1H, brs). |
| 5231 | $C_{23}H_{24}N_4O_5 \cdot HCl$ | 437 (100) | CI | $d_6$-DMSO/400 MHz | 2.15–2.20 (2H, m), 2.80 (6H, s), 3.19–3.26 (2H, m), 4.11 (2H, t), 6.79 (1H, s), 6.83 (1H, s), 7.00 (2H, d), 7.55 (2H, d), 7.69 (1H, t), 7.90 (1H, d), 8.11–8.18 (1H, m), 10.28 (1H, brs), 10.65 (1H, brs), 10.69 (1H, brs). |
| 5232 | $C_{24}H_{24}N_4O_3$ | 417 (100) | CI | $CDCl_3+CF_3CO_2D$/400 MHz | 2.29–2.48 (2H, m), 3.05 (6H, s), 3.43–3.48 (2H, m), 4.15–4.20 (2H, m), 6.96 (2H, d), 7.24 (1H, s), 7.25 (1H, s), 7.44 (2H, d), 7.60–7.78 (4H, m). |
| 5233 | $C_{23}H_{24}ClN_3O_3$ | 428 (33), 426 (100). | CI | $CDCl_3+CF_3CO_2D$/400 MHz | 2.28 (2H, m), 3.00 (6H, s), 3.40 (2H, m), 4.14 (2H, t), 7.00 (2H, d), 7.18 (1H, s), 7.22 (1H, s), 7.38 (2H, d), 7.42 (2H, d), 7.50 (2H, d). |
| 5234 | $C_{24}H_{27}N_3O_4$ | 422 (52) | CI | $CDCl_3+CF_3CO_2D$/400 MHz | 2.30 (2H, m), 3.02 (6H, s), 3.40 (2H, m), 3.89 (3H, s), 4.15 (2H, t), 7.00 (2H, d), 7.04 (2H, d), 7.20 (1H, s), 7.22 (1H, s), 7.40 (2H, d), 7.42 (2H, d). |
| 5235 | $C_{24}H_{27}N_3O_3$ | 406 (28) | CI | $CDCl_3+CF_3CO_2D$/400 MHz | 2.26 (2H, m), 2.40 (3H, s), 3.04 (6H, s), 3.39 (2H, m), 4.15 (2H, t), 6.97 (2H, d), 7.15 (1H, s), 7.18 (1H, s), 7.28 (2H, d), 7.35 (2H, d), 7.40 (2H, d). |
| 5236 | $C_{23}H_{23}Cl_2N_3O_3$ | 464 (4), 462 (24), 460 (36), 216 (31). | CI | $CDCl_3+CF_3CO_2D$/400 MHz | 2.30 (2H, m), 3.03 (6H, s), 3.42 (2H, m), 4.15 (2H, t), 3.98 (2H, d), 6.96 (2H, d), 7.10 (1H, d), 7.23 (1H, s), 7.27 (1H, m), 7.41 (2H, d), 7.52 (1H, m), 7.56 (1H, d). |
| 5237 | $C_{23}H_{24}ClN_3O_3$ | 428 (13), 426 (39). | CI | $d_6$-DMSO/400 MHz | 1.85 (2H, m), 2.14 (6H, s), 2.37 (2H, t), 4.04 (2H, t), 6.73 (1H, s), 6.77 (1H, s), 6.97 (2H, d), 7.34 (1H, m), 7.40 (1H, m), 7.42 (1H, m), 7.50 (2H, d), 7.60 (1H, s), 10.30 (2H, brs). |
| 5238 | $C_{27}H_{33}N_3O_3$ | 448 (54) | CI | $d_6$-DMSO/400 MHz | 1.29 (9H, s), 1.84 (2H, m), 2.15 (6H, s), 2.36 (2H, t), 4.02 (2H, t), 6.71 (2H, s), 6.98 (2H, d), 7.40–7.51 (6H, m), 10.15 (2H, brs). |
| 5239 | $C_{24}H_{24}F_3N_3O_3$ | 460 (62) | CI | $CDCl_3+CF_3CO_2D$/400 MHz | 2.30 (2H, m), 3.05 (6H, s), 3.43 (2H, t), 4.15 (2H, t), 6.96 (2H, d), 7.23 (1H, s), 7.24 (1H, s), 7.41 (2H, d), 7.54 (2H, d), 7.72 (2H, d). |
| 5240 | $C_{23}H_{24}ClN_3O_3 \cdot HCl$ | | | $d_6$-DMSO/400 MHz | 2.16 (2H, m), 2.75 (6H, s), 3.18 (2H, m), 4.10 (2H, t), 6.72 (1H, s), 6.78 (1H, s), 7.00 (2H, d), 7.36 (1H, m), 7.41 (1H, m), 7.43 (1H, m), 7.51 (2H, d), 7.60 (1H, s), 10.21 (1H, s), 10.48 (1H, s), 10.66 (1H, brs). |
| 5241 | $C_{24}H_{27}N_3O_4$ | | | $d_6$-DMSO/400 MHz | 1.83 (2H, m), 2.12 (6H, s), 2.36 (2H, t), 3.85 (3H, s), 4.03 (2H, t), 6.75 (1H, s), 6.85 (1H, s), 7.00 (2H, d), 7.02 (1H, m), 7.09 (1H, d), 7.31 (1H, m), 7.49 (1H, d), 7.51 (2H, d), 9.90 (1H, brs), 10.10 (1H, brs). |
| 5242 | $C_{24}H_{27}N_3O_4$ | | | $CDCl_3+CF_3CO_2D$/400 MHz | 1.95 (2H, m), 2.28 (6H, s), 2.45 (2H, t), 3.83 (3H, s), 4.05 (2H, t), 6.89 (1H, s), 6.92 (1H, s), 7.00 (5H, m), 7.31–7.42 (3H, m). |
| 5245 | $C_{24}H_{24}N_4O_3HCl$ | 417 (100) | ESI | $d_6$-DMSO/400 MHz | 2.10–2.20 (2H, m), 2.80 (6H, s), 3.18–3.25 (2H, m), 4.11 (2H, t), 6.79 (2×1H, s), 7.0 (2H, d), 7.52 (2H, d), 7.70 (2H, d), 7.84 (2H, d), 10.10 (1H, brs), 10.26 (1H, brs), 10.50 (1H, brs). |
| 5246 | $C_{24}H_{28}N_4O_4$ | 435 (100) | CI | $d_6$-DMSO/400 MHz | 1.82–1.88 (2H, m), 2.15 (6H, s), 2.35 (2H, t), 4.05 (2H, t), 6.75 (1H, s), 6.77 (1H, s), 6.98 (2H, d), 7.31 (1H, br), 7.51 (2H, d), 7.62 (2H, d), 7.9 (2H, d), 7.96 (1H, br), 10.23 (1H, brs). |
| 5247 | $C_{25}H_{28}N_4O_4$ | 449 (100) | CI | $d_6$-DMSO/400 MHz | 1.84–1.90 (2H, m), 2.08 (3H, s), 2.15 (6H, s), 2.35 (2H, t), 4.05 (2H, t), 6.69 (1H, s), 6.75 (1H, s), 6.99 (2H, d), 7.20 (2H, d), 7.37 (1H, t), 7.50 (2H, d), 7.61 (2H, d), 7.67 (1H, s), 9.98 (2H, s), 10.05 (1H, brs). |
| 5248 | $C_{25}H_{28}N_4O_4$ | 449 (100) | CI | $d_6$-DMSO/400 MHz | 1.83–1.90 (2H, m), 2.03 (3H, s), 2.17 (6H, s), 2.39 (2H, t), 4.04 (2H, t), 6.72 (1H, s), 6.74 (1H, s), 6.98 (2H, d), 7.16–7.21 (1H, m), 7.29–7.32 (1H, m), 7.46–7.52 (3H, m), 7.60–7.64 (1H, m), 9.52 (1H, brs), 10.03 (1H, brs). |
| 5249 | $C_{23}H_{24}ClN_3O_3$ | 426 (10) | CI | $CDCl_3+CF_3CO_2D$/400 MHz | 2.31 (2H, m), 3.02 (6H, d), 3.42 (2H, m), 4.18 (2H, t), 6.95 (2H, d), 7.20 (1H, s), 7.28 (1H, s), 7.40 (5H, m), 7.55 (1H, m). |
| 5250 | $C_{27}H_{33}N_3O_4$ | | | $CDCl_3+D_2O$/400 MHz | 1.00 (3H, t), 1.50 (2H, m), 1.80 (2H, m), 2.00 (2H, m), 2.25 (6H, s), 2.50 (2H, t), 4.00 (2H, t), 4.05 (2H, t), 6.98–7.04 (6H, m), 7.30–7.40 (4H, m). |
| 5251 | $C_{24}H_{24}F_3N_3O_3$ | 460 (100) | CI | $d_6$-DMSO/400 MHz | 1.82 (2H, m), 2.15 (6H, s), 2.36 (2H, t), 4.01 (2H, t), 6.78 (1H, s), 6.83 (1H, s), 6.98 (2H, d), 7.46–7.58 (3H, m), 7.60–7.72 (2H, m), 7.75 (1H, d). |
| 5252 | $C_{24}H_{24}F_3N_3O_3$ | 460 (52) | CI | $d_6$-DMSO/400 MHz | 1.83 (2H, m), 2.19 (6H, s), 2.38 (2H, t), 4.02 |

-continued

| | | | | | |
|---|---|---|---|---|---|
| | | | | | (2H, t), 6.78 (1H, s), 6.83 (1H, s), 6.98 (2H, d), 7.53 (2H, d), 7.62 (2H, m), 7.79 (1H, d), 7.83 (1H, s), 10.20 (2H, brs). |
| 5254 | $C_{24}H_{26}N_4O_4$·HCl | 435 (100) | CI | $d_6$-DMSO/400 MHz | 2.10–2.19 (2H, m), 2.79 (6H, s), 3.20–3.25 (2H, m), 4.08–4.15 (2H, m), 6.77 (1H, s), 6.79 (1H, s), 7.0 (2H, d), 7.35 (1H, br), 7.55 (2H, d), 7.60 (2H, d), 7.91 (2H, d), 7.99 (1H, br), 10.19 (1H, brs), 10.32 (1H, brs). |
| 5255 | | 537 (70), 407 (50), 166 (35), 86 (100). | CI | $d_6$-DMSO/400 MHz | |
| 5256 | $C_{25}H_{28}N_4O_4$·HCl | 449 (100) | CI | $d_6$-DMSO/400 MHz | 2.05 (3H, s), 2.18–2.28 (2H, m), 2.78 (6H, s), 3.15–3.25 (2H, m), 4.11 (2H, t), 6.69 (1H, s), 6.75 (1H, s), 7.0 (2H, d), 7.18–7.20 (1H, m), 7.34 (1H, t), 7.55 (2H, d), 7.59–7.62 (1H, m), 7.69 (1H, s), 9.48 (2H, brs), 10.15 (1H, brs). |
| 5259 | $C_{25}H_{28}N_4O_4$·HCl | 449 (100) | CI | $d_6$-DMSO/400 MHz | 2.01 (3H, s), 2.11–2.18 (2H, m), 2.77 (6H, s), 3.19–3.25 (2H, m), 4.11 (2H, t), 6.74 (1H, s), 6.76 (1H, s), 7.0 (2H, d), 7.18–7.22 (1H, m), 7.28–7.33 (1H, m), 7.48–7.50 (1H, m), 7.53 (2H, d), 7.56–7.60 (1H, m), 9.41 (1H, brs), 9.89 (1H, brs), 10.09 (1H, brs), 10.18 (1H, brs). |
| 5260 | $C_{23}H_{26}N_4O_3$ | 407 (70) | CI | $d_6$-DMSO/400 MHz | 1.80–1.90 (2H, m), 2.18 (6H, s), 2.39 (2H, t), 4.03 (2H, t), 5.52 (2H, s), 6.60 (2H, d), 6.65 (1H, s), 6.69 (1H, s), 6.98 (2H, d), 7.28 (2H, d), 7.48 (2H, d), 9.80 (1H, brs), 11.58 (1H, brs). |
| 5343 | $C_{30}H_{30}N_4O_4$ | 511 (10) | CI | $d_6$-DMSO/400 MHz | 1.85 (2H, m), 2.45 (6H, s), 2.37 (2H, t), 4.05 (2H, t), 4.05 (2H, t), 6.78 (1H, s), 6.81 (1H, s), 6.99 (2H, d), 7.10 (1H, m), 7.35 (2H, m), 7.52 (2H, d), 7.70 (2H, d), 7.79 (2H, d), 8.01 (2H, d), 10.2–10.3 (3H, br). |
| 5344 | $C_{31}H_{32}N_4O_4$ | 525 (10) | CI | $d_6$-DMSO/400 MHz | 1.85 (2H, m), 2.15 (6H, s), 2.35 (2H, t), 4.05 (2H, t), 4.49 (2H, d), 6.76 (1H, s), 6.78 (1H, s), 6.97 (2H, d), 7.22 (1H, m), 7.32 (4H, m), 7.50 (2H, d), 7.61 (2H, d), 7.91 (2H, d), 9.05 (1H, t), 10.2–10.4 (2H, br). |
| 5345 | $C_{32}H_{34}N_4O_4$ | 539 (100) | CI | $d_6$-DMSO/400 MHz | 1.85 (2H, m), 2.15 (6H, s), 2.35 (2H, t), 2.85 (2H, t), 3.49 (2H, m), 4.05 (2H, t), 6.76 (1H, s), 6.78 (1H, s), 6.99 (2H, d), 7.18–7.32 (5H, m,), 7.52 (2H, d), 7.61 (2H, d), 7.85 (2H, d), 8.55 (1H, brt), 10.20 (2H, br). |
| 5346 | $C_{33}H_{36}N_4O_4$ | 553 (5) | CI | $d_6$-DMSO/400 MHz | 1.76–1.86 (4H, m), 2.15 (6H, s), 2.34 (2H, t), 2.62 (2H, t), 3.30 (2H, m), 4.02 (2H, t), 6.73 (1H, s), 6.76 (1H, s), 6.96 (2H, d), 7.12–7.28 (5H, m), 7.49 (2H, d), 7.59 (2H, d), 7.86 (2H, d), 8.45 (1H, brt), 10.20 (2H, br). |
| 5347 | $C_{34}H_{36}N_4O_4$ | 567 (5) | CI | $d_6$-DMSO/400 MHz | 1.52–1.65 (4H, m), 1.85 (2H, m), 2.15 (6H, s), 2.35 (2H, t), 2.61 (2H, t), 3.30 (2H, m), 4.02 (2H, t), 6.73 (1H, s), 6.76 (1H, s), 6.96 (2H, d), 7.12–7.27 (5H, m), 7.50 (2H, d), 7.61 (2H, d), 7.86 (2H, d), 8.43 (1H, brt), 10.20 (2H, br). |
| 5348 | $C_{24}H_{24}N_4O_3$ | 417 (100) | CI | $CDCl_3$/400 MHz | 2.26–2.35 (2H, m), 3.01 (6H, s), 3.39–3.45 (2H, m), 4.17–4.20 (2H, t), 6.96 (2H, d), 7.20 (1H, s), 7.25 (1H, s), 7.40 (2H, d), 7.55 (2H, d), 7.76 (2H, d). |
| 5360 | $C_{23}H_{24}BN_3O_3$ | 472 (100), 470 (100). | ESI | $d_6$-DMSO/400 MHz | 1.80–1.91 (2H, m), 2.12 (6H, s), 2.30–2.38 (2H, m), 4.00–4.08 (2H, m), 6.69 (1H, s), 6.74 (1H, s), 6.99 (2H, d), 7.45–7.52 (4H, m), 7.59 (2H, d), 10.19 (1H, brs). |
| 5360.HCl | $C_{23}H_{24}BrN_3O_3$·HCl | 471 (100) | CI | $d_6$-DMSO/400 MHz | 2.10–2.20 (2H, m), 2.79 (6H, s), 3.19–3.25 (2H, m), 4.09–4.25 (2H, m), 6.70 (1H, s), 6.75 (1H, s), 7.0 (2H, d), 7.45–7.80 (6H, m), 9.38 (1H, brs), 10.15 (1H, brs), 10.30 (1H, brs). |
| 5365 | $C_{23}H_{24}FN_3O_3$ | 410 (100) | ESI | $CDCl_3$+$CF_3CO_2D$/400 MHz | 2.28–2.35 (2H, m), 3.05 (6H, s), 3.41–3.48 (2H, m), 4.18–4.21 (2H, m), 6.96 (2×1H, s), 7.13–7.27 (4H, m), 7.39–7.48 (4H, m). |
| 5365.HCl | $C_{23}H_{24}FN_3O_3$·HCl | 410 (100) | ESI | $d_6$-DMSO/400 MHz | 2.10–2.20 (2H, m), 2.79 (6H.2), 3.09 (2H, m), 4.09 (2H, t), 6.75 (2H, s), 7.0 (2H, d), 7.24 (2H, t), 7.55 (2H, d), 7.58–7.61 (2H, m), 10.12 (1H, br.s), 10.25 (1H, brs). |
| 5366 | $C_{23}H_{24}ClN_3O_3$ | 416 (100) | ESI | $CDCl_3$+$CF_3CO_2D$/400 MHz | 2.29–2.35 (2H, m), 3.03 (6H, s), 3.45 (2H, t), 4.19 (2H, t), 6.97 (2H, d), 7.21 (1H, s), 7.26 (1H, s), 7.37–7.42 (4H, m), 7.48 (2H, d). |
| 5375 | $C_{23}H_{24}BrN_3O_3$ | 472 (50), 470 (50). | CI | $d_6$-DMSO/400 MHz | 1.83 (2H, m), 2.15 (6H, s), 2.35 (2H, t), 4.02 (2H, t), 6.70 (1H, s), 6.75 (1H, s), 6.97 (2H, d), 7.35 (1H, m), 7.50 (4H, m), 7.69 (1H, s), |

| | | | | | |
|---|---|---|---|---|---|
| 5373 | $C_{23}H_{24}FN_3O_3$ | 410 (100) | CI | $d_6$-DMSO/400 MHz | 10.30 (2H, br.). 1.85 (2H, m), 2.15 (6H, s), 2.35 (2H, t), 4.03 (2H, t), 6.75 (1H, s), 6.77 (1H, s), 6.99 (2H, d), 7.14 (1H, m), 7.32–7.47 (3H, m), 7.50 (2H, d), 10.20 (2H, br). |
| 5374 | $C_{24}H_{24}F_3N_3O_4$ | 476 (100) | CI | $d_6$-DMSO/400 MHz | 1.85 (2H, m), 2.15 (6H.2), 2.35 (2H, t), 4.02 (2H, t), 6.75 (2×1H, s), 6.97 (2H, d), 7.29 (1H, m), 7.49–7.52 (5H, m), 10.20 (2H, br). |
| 5378 | $C_{23}H_{23}N_5O_7$ | 482 (100) | CI | $d_6$-DMSO/400 MHz | 1.80–1.90 (2H, m), 2.15 (6H, s), 2.47 (2H, t), 4.05 (2H, m), 6.75 (1H, s), 6.85 (1H, s), 6.95 (2H, d), 7.50 (2H, d), 8.70 (3H, m). |
| 5380 | $C_{23}H_{23}Cl_2N_3O_3 \cdot HCl$ | | | $d_6$-DMSO/400 MHz | 2.15 (2H, m), 2.77 (6H, s), 3.20 (2H, t), 4.10 (2H, t), 6.70 (1H, s), 6.78 (1H, s), 7.00 (2H, d), 7.50–7.55 (5H, m), 10.10 (1H, brs), 10.25 (1H, brs), 10.65 (1H, brs). |
| 5381 | $C_{23}H_{23}N_5O_7 \cdot HCl$ | | | $d_6$-DMSO/400 MHz | 2.10–2.15 (2H, m), 2.80 (6H, s), 3.20 (2H, t), 4.10 (2H, t), 6.80 (1H, s), 6.90 (1H, s), 7.00 (2H, d), 7.54 (2H, d), 8.65–8.75 (3H, m), 10.30 (1H, brs), 10.90 (1H, brs). |
| 5385 | $C_{24}H_{27}N_2O_3S$ | 438 (100) | ESI | $CDCl_3 + CF_3CO_2D$/400 MHz | 2.19–2.37 (2H, m), 2.52 (3H, m), 2.56 (6H, s), 3.43–3.49 (2H, m), 4.18–4.21 (2H, m), 6.96 (2H, d), 7.25 (2×1H, s), 7.32–7.46 (6H, m). |
| 5385.HCl | $C_{24}H_{27}N_2O_3 \cdot HCl$ | 438 (100) | ESI | $d_6$-DMSO/400 MHz | 2.08 (3H, s), 2.10–2.17 (2H, m), 2.81 (6H, d), 4.11 (2H, t), 6.73 (1H, s), 6.75 (1H, s), 7.00 (2H, d), 7.30 (2H, d), 7.50 (2H, d), 7.52 (2H, d), 9.76 (1H, brs), 10.10 (1H, brs), 10.18 (1H, brs). |
| 5398 | $C_{23}H_{21}ClN_4O_5$ | | | $CDCl_3 + CF_3CO_2D$/400 MHz | 2.29–2.35 (2H, m), 3.05 (6H, s), 3.42–3.49 (2H, m), 4.17–4.21 (2H, m), 6.98 (2H, d), 7.18 (1H, s), 7.29 (1H, s), 7.43 (2H, d), 7.55–7.60 (1H, dd), 7.68 (1H, d), 7.97 (1H, d). |
| 5398.HCl | $C_{23}H_{21}ClN_4O_5 \cdot HCl$ | | | $d_6$-DMSO/400 MHz | 2.09–2.19 (2H, m), 2.72 (6H, s), 3.18 (2H, t), 4.11 (2H, t), 6.78 (1H, s), 6.80 (1H, s), 7.00 (2H, d), 7.55 (2H, d), 7.78 (2H, s), 8.18 (1H, s), 10.25 (1H, brs), 10.64 (1H, brs). |
| 5401 | $C_{25}H_{27}N_3O_5$ | 450 (20) | CI | $d_6$-DMSO/400 MHz | 1.85 (2H, m), 2.15 (6H, s), 2.35 (2H, t), 3.85 (3H, s), 4.05 (2H, t), 6.75 (1H, s), 6.77 (1H, s), 6.97 (2H, d), 7.50 (2H, d), 7.65 (2H, d), 7.95 (2H, d), 10.25 (2H, brs). |
| 5401.HCl | $C_{25}H_{27}N_3O_5 \cdot HCl$ | | | $d_6$-DMSO/400 Mz | 2.10–2.20 (2H, m), 2.80 (6H, s), 3.20–3.25 (2H, m), 3.86 (3H, s), 4.12 (2H, t), 6.78 (1H, s), 6.80 (1H, s), 7.00 (2H, d), 7.55 (2H, d), 7.65 (2H, d), 7.95 (2H, d), 10.10 (1H, brs), 10.22 (1H, brs), 10.40 (1H, brs). |

We claim:

1. A compound which is selected from the group consisting of a diketopiperazine of formula (A):

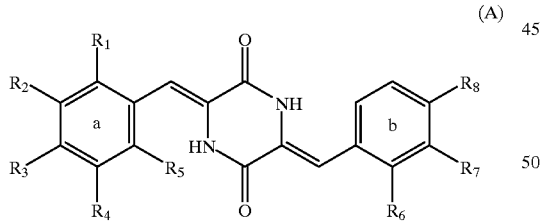

(A)

wherein
$R_1$ is H, Cl or —COOMe; $R_2$, $R_3$ and $R_4$ are each independently H or —O(CH$_2$)$_n$NMe$_2$ wherein n is 1 or 2;
$R_5$ is H or Cl;
$R_6$ is H or F;
$R_7$ is H, OMe or —O(CH$_2$)$_n$ NMe$_2$ wherein n is 1 or 2; and
$R_8$ is H, F or —O(CH$_2$)$_n$NMe$_2$; and the pharmaceutically acceptable salts thereof; with the exception of compounds wherein each of $R_1$ to $R_8$ is H.

2. A compound which is selected from the group consisting of a diketopiperazine of formula (A):

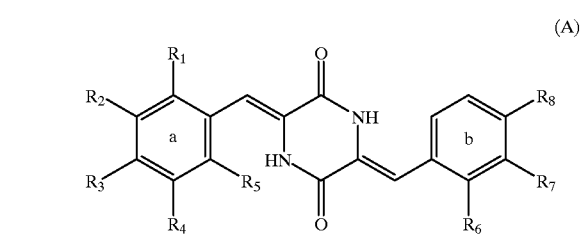

(A)

wherein each of $R_1$ to $R_5$ is H;
$R_6$ H, —O(CH$_2$)$_n$NMe$_2$, Cl or F;
$R_7$ is H, —O(CH$_2$)$_n$NMe$_2$ wherein n is 1 to 2, or OMe; and
$R_8$ is H, —OCOCH$_2$—$^t$Bu, —O(CH$_2$)$_n$NMe$_2$ wherein n is 1 or 2, —CH$_2$NH$_2$, —CH$_2$N[(CH$_2$)$_3$NMe$_2$]$_2$ or —OCH$_2$CO$_2$H; and the pharmaceutically acceptable salts thereof; with the exception of compounds wherein each of $R_1$ to $R_8$ is H.

3. A compound according to claim 2 which is a salt with hydrochloric acid, trifluoroacetic acid, methanesulphonic acid, sulphuric acid, orthophosphoric acid, p-toluenesulphonic acid, or is a sodium or potassium salt.

4. A compound selected from:
(3Z,6Z)-3,6-Di-(4-(2-dimethylaminoethoxy) benzylidene)-2,5-piperazinedione dihydrochloride;

(3Z,6Z)-3-Benzylidene-6-(4-bis(2-dimethylaminopropyl) aminomethylbenzylidene-2,5-piperazinedione;

(3Z,6Z)-3-Benzylidene-6-(4-(2-dimethylaminoethoxy) benzylidene)-2,5-piperazinedione;

(3Z,6Z)-3,6-Di-(4-(2-dimethylaminopropoxy) benzylidene)-2,5-piperazinedione bis methan sulfonate (1:2);

(3Z,6Z)-3-Benzylidene-6-(3,4-di-(2-dimethylamnoethoxy)benzylidene)-2,5-piperazinedione;

(3Z,6Z)-3-(2,6-Dichlorobenzylidene)-6-(4-(2-dimethylaminoethoxy)benzylidene-2,5-piperazinedione;

(3Z,6Z)-3,6-Di-(4-(3-dimethylaminopropoxy) benzylidene)-2,5-piperazinedione bis hydrogen succinate (1:2);

(3Z,6Z)-3-Benzylidene-6-(4-dimethylaminomethylbenzylidene)-2,5-piperazinedione;

Methyl 4-(4-((3Z,6Z)-6-(4-Methoxybenzylidene)-2,5-dioxo-3-piperazinylidene)methylbenzylcarbonyl) butanoate;

(3Z,6Z)-3-(4-(3,3-dimethylbutanoyloxy)benzylidene)-6-(4-methoxybenzylidene)-2,5-piperazinedione;

(3Z,6Z)-3-(4-Acetamidobenzylidene)-6-(2-fluorobenzylidene)-2,5-piperazinedione;

(3Z,6Z)-3-Benzylidene-6-(2-chloro-4-(2-dimethylaminoethoxy)benzylidene)-2,5-piperazinedione;

(3Z,6Z)-3-Benzylidene-6-(2,4-di-(2-dimethylaminopropoxy)benzylidene)-2,5-piperazinedione;

(3Z,6Z)-3-Benzylidene-6-(2,4-di-(2-dimethylaminoethoxy)benzylidene-2,5-piperazinedione;

(3Z,6Z)-3-Benzylidene-6-(4-bis(3-dimethylaminopropyl) aminomethylbenzylidene)-2,5-piperazinedione;

(3Z,6Z)-3-Benzylidene-6-(4-(2-dimethylaminoethoxy) benzylidene)-2,5-piperazinedione;

(3Z,6Z)-3-(2,4-Difluorobenzylidene)-6-(4-(2-dimethylaminoethoxy)benzylidene)-2,5-piperazinedione;

(3Z,6Z)-3-(4-(2-Dimethylaminoethoxy)benzylidene)-6-(4-methoxybenzylidene-2,5-piperazinedione;

(3Z,6Z)-3-Benzylidene-6-(2-(2-dimethylaminoethoxy) benzylidene)-2,5-piperazinedione;

(3Z,6Z)-3-Benzylidene-6-(4-(2-dimethylaminoethoxy) benzylidene)-2,5-piperazinedione;

(3Z,6Z)-3-(4-Aminomethylbenzylidene)-6-benzylidene-2,5-piperazinedione trifluoroacetate;

(3Z,6Z)-3-Benzylidene-6-(4-dimethylaminobenzylidene)-2,5-piperazinedione hydrochloride; and (3Z,6Z)-3-(4-Hexyloxybenzylidene)-6-(4-methoxybenzylidene)-2,5-piperazinedione.

5. A pharmaceutical or veterinary composition comprising a pharmaceutically or veterinarily acceptable carrier or diluent and, as an active principle, a compound as claimed in claim 2.

6. A method of treating a patient suffering from a thrombotic disease, thrombotic disorder or hemostatic disorder, the said disease or disorder being associated with elevated levels of PAI-1, which method comprises administering to the patient a therapeutically effective amount of a compound selected from the group consisting of a diketopiperazine of formula (A):

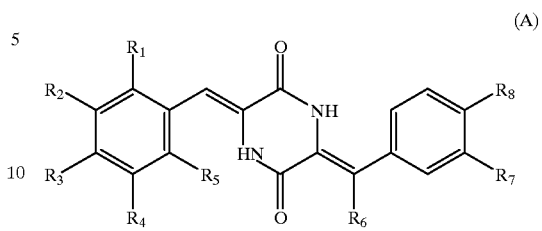

wherein
$R_1$ is H, a halogen, —$COOR_{11}$, $C_1$–$C_6$ alkyl, $NO_2$, $C_1$–$C_6$ alkoxy, —$NHCOCH_3$ or $CF_3$;

$R_2$ is H, —$O(CH_2)_nN(R_{11}R_{12})$, $C_1$–$C_6$ alkyl, $NO_2$, CN, halogen, $C_1$–$C_6$ alkoxy, $CF_3$, $OCF_3$, —$NHCOCH_3$ or phthalimido;

$R_3$ is H, —$O(CH_2)_nN(R_{11}R_{12})$, halogen, $C_1$–$C_6$ alkoxy, $NO_2$, $C_1$–$C_6$ alkyl, $CF_3$, CN, —$CON(R_{11}R_{12})$, —$NHCOCH_3$, —$CO_2R_{11}$, —$CONH(CH_2)_nPh$, $SR_{13}$ or —$(CH_2)_nN(R_{11}R_{12})$; or $R_2$ and $R_3$ together form a methylenedioxy group —$OCH_2O$—;

$R_4$ is H, halogen, $NO_2$ or —$O(CH_2)_nN(R_{11}R_{12})$;

$R_5$ is H or a halogen;

$R_6$ is H, a halogen or —$O(CH_2)_nN(R_{11}R_{12})$;

$R_7$ is H, —$O(CH_2)_nN(R_{11}R_{12})$ or $C_1$–$C_6$ alkoxy; and $R_8$ is H, a halogen, —$O(CH_2)_nN(R_{11}R_{12})$, —$CH_2Y(CH_2)_n N(R_{11}R_{12})$, —$OC(O)(CH_2)_nR_{11}$, $C_1$–$C_6$ alkoxy, —$CH_2NHCO(CH_2)_nCO_2R_{11}$, —$(CH_2)_nN(R_{11}R_{12})$, —$CH_2N[(CH_2)_nN(R_{11}R_{12})]_2$, or —$O(CH_2)_nCO_2H$ wherein n is 0 or an integer of 1 to 6, Y is O or S, each of $R_{11}$ and $R_{12}$ is, independently, hydrogen or a straight or branched $C_1$–$C_6$ alkyl and $R_{13}$ is straight or branched $C_1$–$C_6$ alkyl; the pharmaceutically acceptable salts thereof and the pharmaceutically acceptable esters thereof selected from the group consisting of branched and unbranched, saturated and unsaturated $C_1$–$C_6$ alkyl esters; with the exception of compounds wherein:

(i) each of $R_1$ to $R_8$ is H;

(ii) $R_1$ and $R_2$ are both Cl, Br or F and the rest of $R_1$ to $R_8$ are H; $R_3$ and $R_8$ are both the same and are both F, Cl, I, OMe or $NMe_2$ and the rest of $R_1$ to $R_8$ are H; and (iii) $R_8$ is OMe and the rest of $R_1$ to $R_8$ are H.

7. A method of treating a patient suffering from a thrombotic disease or thrombotic disorder, the said disease or disorder being associated with elevated levels of PAI-1, which method comprises administering to the patient a therapeutically effective amount of a compound as claimed in claim 4, 1 or 2.

8. A method of treating a patient suffering from a hemostatic disorder associated with elevated levels PAI-1, which method comprises administering to the patient a therapeutically effective amount of a compound as claimed in claim 4, 1 or 2.

9. A method according to claim 7 wherein the patient is suffering from myocardial infarction, deep vein thrombosis or disseminated intravascular coagulation.

10. A method according to claim 6 wherein, in formula (A), $R_1$ is H, Cl, Me, MeO, $NO_2$ or —COOMe;

$R_2$ is H, Me, MeO, Cl, Br or —$O(CH_2)_nNMe_2$; or $R_2$ and $R_3$ together form a methylenedioxy group —$OCH_2O$—;

$R_3$ is H, $OCH_3$, $OC_6H_{13}$, $O(CH_2)_nNMe_2$ wherein n is 2 or 3, or $CH_2NMe_2$;

$R_4$ is H or —$O(CH_2)_2NMe_2$;

$R_5$ is H or Cl, $R_6$ is H, Cl or F or —$O(CH_2)_2NMe_2$;

$R_7$ is H, —$O(CH_2)_nNMe_2$ wherein n is 1 or 2, or OMe; and $R_8$ is H, F, OMe, —$O(CH_2)_nNMe$, —$CH_2S(CH_2)_nNMe_2$ or —$CH_2O(CH_2)_nNMe_2$ wherein n is 1, 2 or 3, —$CH_2NHCO(CH_2)_3CO_2Me$, —$CH_2NH_2$, —$(CH_2)_nNMe_2$ wherein n is 1, 2, 3 or 4; —$OCH_2CO_2H$, —$CH_2N[CH_2)_3NMe_2]$ or —$OCO(CH_2)_nR_{11}$ wherein n is from 1 to 5 and $R_{11}$ is $CH_3$ or t-butyl.

11. A method according to claim 6 wherein, in formula (A), each of $R_1$ to $R_5$ is H;

$R_6$ is H, —$O(CH_2)_nNMe_2$, Cl or F;

$R_7$ is H, —$O(CH_2)_nNMe_2$ wherein n is 1 or 2, or OMe; and $R_8$ is H, —$OCOCH_2$—$^tBu$, —$O(CH_2)_nNMe_2$ wherein n is 1 or 2, —$CH_2NH_2$, —$CH_2N[(CH_2)_3NMe_2]_2$ or —$OCH_2CO_2H$.

12. A method according to claim 6 wherein, in formula (A), $R_1$ is H, Cl or —COOMe;

$R_2$, $R_3$ and $R_4$ are each independently H or —$O(CH_2)_nNMe_2$ wherein n is 1 or 2;

$R_5$ is H or Cl;

$R_6$ is H or F;

$R_7$ is H, OMe or —$O(CH_2)_nNMe_2$ wherein n is 1 or 2; and $R_8$ is H, F, or —$O(CH_2)_2NMe$.

13. A method according to claim 6 wherein, in formula (A), each of $R_6$ and $R_7$ is hydrogen and $R_8$ is —$O(CH_2)_nN(R_{11}R_{12})$ or —$CH_2Y_{(CH)_n}N(R_{11}R_{12})$.

14. A method according to claim 6 wherein the patient is suffering from myocardial infarction, deep vein thrombosis or disseminated intravascular coagulation.

* * * * *